United States Patent [19]

Alpegiani et al.

[11] Patent Number: 4,729,990
[45] Date of Patent: Mar. 8, 1988

[54] SUBSTITUTED PENEM DERIVATIVES

[75] Inventors: Marco Alpegiani; Angelo Bedeschi; Maurizio Foglio; Giovanni Francheschi; Ettore Perrone, all of Milan, Italy

[73] Assignee: Farmitalia Carlo Erba S.p.A., Milan, Italy

[21] Appl. No.: 807,688

[22] Filed: Dec. 11, 1985

Related U.S. Application Data

[62] Division of Ser. No. 481,924, Apr. 4, 1983, Pat. No. 4,577,016.

[30] Foreign Application Priority Data

Apr. 8, 1982 [GB] United Kingdom ................ 8210410

[51] Int. Cl.4 .................. C07D 499/00; A61K 31/425
[52] U.S. Cl. ...................................... 514/192; 540/310; 540/350
[58] Field of Search ................ 260/245.2 R; 540/310; 514/192

[56] References Cited

U.S. PATENT DOCUMENTS

| | | | |
|---|---|---|---|
| 4,269,771 | 5/1981 | Lombardi et al. | 260/245.2 |
| 4,272,437 | 6/1981 | Menard et al. | 540/310 |
| 4,282,150 | 9/1979 | Menard et al. | 260/245.2 |
| 4,301,074 | 11/1981 | Christensen et al. | 260/245.2 |
| 4,331,677 | 5/1982 | Foglio et al. | 424/270 |
| 4,386,029 | 5/1983 | Corbett | 260/245.2 |
| 4,435,412 | 3/1984 | Girijavallabhan et al. | 424/270 |
| 4,482,565 | 11/1984 | Foglio et al. | 260/245.2 R |
| 4,508,649 | 4/1982 | Alpegiani et al. | 260/245.2 |
| 4,558,042 | 12/1985 | Foglio et al. | 514/192 |
| 4,585,874 | 4/1986 | Alpegiani et al. | 546/272 |

FOREIGN PATENT DOCUMENTS

| | | |
|---|---|---|
| 881862 | 2/1979 | Belgium . |
| 13067 | 7/1980 | European Pat. Off. . |
| 69373 | 1/1983 | European Pat. Off. . |
| 57-179190 | 12/1981 | Japan . |
| 7909056 | 6/1980 | Netherlands . |
| 7909055 | 6/1980 | Netherlands . |
| 2013674A | 2/1978 | United Kingdom . |
| 2013674 | 10/1979 | United Kingdom . |
| 2043639 | 7/1980 | United Kingdom . |
| 2042514 | 12/1980 | United Kingdom . |
| 2097786 | 9/1981 | United Kingdom . |
| 2118181 | 1/1983 | United Kingdom . |

Primary Examiner—Nicholas S. Rizzo
Attorney, Agent, or Firm—Oblon, Fisher, Spivak, McClelland & Maier

[57] ABSTRACT

Antibacterial compounds of formula (I)

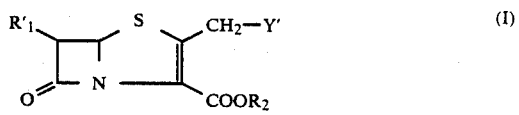

wherein, $R_1'$ is alkyl or hydroxyalkyl;

$R_2$ is hydrogen or a carboxy protecting group; and $Y'$ is a group-S-heterocyclic or pyridyl, which group may be substituted, and pharmaceutically or veterinarily acceptable salts thereof and pharmaceutical compositions containing the same.

9 Claims, No Drawings

SUBSTITUTED PENEM DERIVATIVES

This is a division of application Ser. No. 481,924, filed Apr. 4, 1983 now U.S. Pat. No. 4,577,016.

The present invention relates to a new process for the preparation of substituted penems and to new penem compounds and process for their preparation and pharmaceutical and veterinary compositions containing them. A first object of the invention is a new process for the preparation of compounds of formula (I)

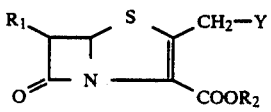

wherein
$R_1$ is hydrogen or an organic group;
$R_2$ is hydrogen or a carboxy protecting group; and
Y is
(a) a group —S-Het wherein Het is an optionally substituted saturated or unsaturated heterocyclic ring containing at least one heteroatom chosen from O, S and N;
(b) a formyloxy or a $C_2$–$C_6$ carboxylic acyloxy group wherein the acyl group may be unsubstituted or substituted by halogen, $C_2$–$C_6$ carboxylic acyl, amino, hydroxy or mercapto and wherein the amino, hdyroxy and mercapto groups may optionally be in a protected form;
(c) a $C_1$–$C_{12}$ alkoxy or $C_1$–$C_{12}$ alkylthio group both optionally substituted by one or more substituents chosen from halogen, formyl, $C_2$–$C_6$ acyl, amino, hydroxy and mercapto, wherein the amino, hydroxy and mercapto groups may optionally be in a protected form;
(d) an optionally substituted pyridyl group; or
(e) azido; and the pharmaceutically or veterinarily acceptable salts of the compounds of formula (I). Another object of the invention concerns new penem derivatives falling within the scope of formula (I) and pharmaceutically or veterinarily acceptable salts thereof, a process for their preparation, and pharmaceutical or veterinary compositions containing said new penem derivatives.

In the above formula (I) the organic group $R_1$ is especially an optionally substituted aliphatic or cycloaliphatic hydrocarbon group. When $R_1$ is an aliphatic hydrocarbon group it is preferably a $C_1$–$C_{12}$ alkyl group, optionally substituted by one or more substituents chosen from hydroxy, amino, cyano and mercapto, wherein the hydroxy, amino and mercapto groups may be free or protected.

Preferred alkyl groups for $R_1$ are methyl and ethyl, in particular ethyl, and a particularly preferred substituent on such groups is an optionally protected hydroxy. When $R_1$ is a cycloaliphatic hydrocarbon group it is, preferably, a $C_4$–$C_7$ monocycloalkyl group, in particular cyclopentyl or cyclohexyl, optionally substituted by one or more substituents chosen from $C_1$–$C_6$ alkyl, for example methyl or ethyl, hydroxy, amino, cyano, and mercapto groups, the hydroxy, amino and mercapto groups being free or protected.

When $R_2$ is a carboxy protecting group it may be any group which, together with the —COO— moiety, forms an esterified carboxy group. Examples of carboxy protecting groups $R_2$ are, in particular, $C_1$–$C_6$ alkyl groups, for instance methyl, ethyl or tert-butyl; halo-substituted $C_1$–$C_6$ alkyl groups, for example 2,2,2-trichloroethyl; $C_2$–$C_4$ alkenyl groups, for example allyl; optionally substituted aryl groups, for example phenyl and p-nitro-phenyl; optionally substituted aryl-$C_1$–$C_6$ alkyl groups, for example benzyl, p-nitro-benzyl and p-methoxy-benzyl; aryloxy-$C_1$–$C_6$ alkyl groups, for example phenoxy-methyl; or groups such as benzhydryl, o-nitro-benzhydryl, acetonyl, trimethylsilyl, diphenyl-tert-butyl-silyl, and dimethyl-tert-butyl-silyl.

The definition of $R_2$ as a carboxy protecting group includes also any residue, such as for instance acetoxymethyl, pivaloyloxymethyl or phtalidyl, leading to an ester group which is known to be hydrolized "in vivo" and to have favourable pharmacokinetic properties. When Y is a group —S-Het as defined above, the group Het is, especially:

(A) a pentatomic or hexatomic heteromonocyclic ring, containing at least one double bond and at least one heteroatom selected from N, S and O, unsubstituted or substituted by one or more substituents selected from:

(a') hydroxy, $C_1$–$C_6$ alkoxy, halogen, $C_2$–$C_6$ aliphatic acyl;

(b') $C_1$–$C_6$ alkyl unsubstituted or substituted by a tetrazolyl group or by one or more substituents selected from hydroxy and halogen;

(c') $C_2$–$C_6$ alkenyl unsubstituted or substituted by one or more substituents selected from hydroxy and halogen;

(d') —S—$R_3$ wherein $R_3$ is hydrogen or $C_1$–$C_6$ alkyl; or —S—$CH_2$—$COOR_4$ wherein $R_4$ is hydrogen, $C_1$–$C_6$ alkyl or a carboxy-protecting group;

(e') —$(CH_2)_m$—$COOR_4$ or —CH=CH—$COOR_4$ wherein m is zero, 1, 2 or 3 and $R_4$ is as defined above; —$(CH_2)_m$—CN or —$(CH_2)_m$—$CONH_2$ wherein m is as defined above; —$(CH_2)_m$—$SO_3H$ wherein m is as defined above or (f')

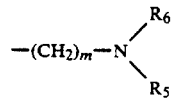

wherein m is as defined above, and each of $R_5$ and $R_6$, which may be the same or different, represents hydrogen, $C_1$–$C_6$ alkyl, sulpho, or an aliphatic acyl group or, when one of $R_5$ and $R_6$ is hydrogen, the other may be also an amino protecting group; or (B) a heterobicyclic ring, containing at least two double bonds wherein each of the condensed heteromonocyclic rings, being the same or different, is a pentatomic or hexatomic heteromonocyclic ring containing at least one heteroatom selected from N, S and O, said heterobicyclic ring being unsubstituted or substituted by one or more substituents selected from (a'), (b'), (c'), (d'), (e') and (f') as defined above.

In the above definitions (A) and (B), preferred halogens are chlorine, bromine and iodine; preferred $C_1$–$C_6$ alkyl groups are methyl and ethyl; a preferred $C_2$–$C_6$ alkenyl group is allyl; a preferred aliphatic acyl group is acetyl; a carboxy protecting group may be any of the groups previously indicated for the $R_2$ substituent; and the free sulpho and carboxy groups possibly present may be salified, e.g. as sodium or potassium salts.

A heteromonocyclic ring of the above class (A) may be, for example, an optionally substituted thiazolyl, triazolyl, thiadiazolyl, tetrazolyl, imidazolyl, pyrazinyl or triazinyl ring. Preferred substituents on such rings are, for example, one or more substituents chosen from amino, hydroxy, oxo, —S—CH$_2$—COOH, a C$_1$-C$_6$ alkoxy and a C$_1$-C$_6$-alkyl group, preferably methyl or ethyl, wherein the C$_1$-C$_6$-alkyl group may be optionally substituted by a substituent chosen from carboxy, sulpho, cyano, carbamoyl, amino, methylamino, dimethylamino or sulfoamino.

A heterobicyclic ring of the above class (B) may be, for example, a tetrazolopyridazinyl radical optionally substituted by amino or carboxy. When Y is a C$_2$-C$_6$ carboxylic acyloxy group, the acyl group is, preferably, a C$_2$-C$_6$ aliphatic acyl, in particular acetyl, either unsubstituted or in its turn substituted by a C$_2$-C$_6$ acyl group, preferably an aliphatic acyl, in particular acetyl.

When Y is a C$_1$-C$_{12}$ alkoxy or C$_1$-C$_{12}$ alkylthio group, C$_1$-C$_6$ alkoxy and C$_1$-C$_6$ alkylthio groups are preferred, in particular methoxy, ethoxy, methylthio and ethylthio, optionally substituted as reported above. A particularly preferred substituted C$_1$-C$_6$ alkylthio group is, for example, ethylthio substituted by amino.

When Y is unsubstituted pyridyl it is, preferably, 1-pyridyl.

When Y is a substituted pyridyl group it is, preferably, a 1-pyridyl group substituted by carbamoyl, in particular 4-carbamoyl.

In the above formula (I) the amino, hydroxy or mercapto protecting groups possibly present may be those usually employed in the chemistry of penicillins and cephalosporins for this kind of functions. They may be, for instance, optionally substituted, especially halo-substituted, acyl groups, e.g. acetyl, monochloroacetyl, dichloroacetyl, trifluoroacetyl, benzoyl or p-bromophenacyl; triarylmethyl groups, in particular triphenylmethyl; silyl groups, in particular trimethylsilyl, dimethyl-tert-butyl-silyl, diphenyl-tert-butyl silyl; or also groups such as tert-butoxy carbonyl, p-nitro-benzyloxycarbonyl, 2,2,2-trichloroethoxycarbonyl, benzyl, and pyranyl. When, in particular, the R$_1$ substituent in formula (I) is an alkyl group substituted by hydroxy, preferred protecting groups of the hydroxy function are p-nitrobenzyloxycarbonyl; dimethyl-tert-butyl silyl; diphenyl-tert-butyl silyl; trimethyl silyl; 2,2,2-trichloroethoxycarbonyl; benzyl; p-bromo-phenacyl; triphenylmethyl and pyranyl. All the alkyl and alkenyl groups, including the aliphatic hydrocarbon moiety of the alkoxy, alkylthio and acyloxy groups, may be branched or straight. As already reported, also the pharmaceutically or veterinarily acceptable salts of the compound of formula (I) may be prepared according to the process of the invention. The said salts may be both salts with acids, either inorganic acids such as, e.g., hydrochloric or sulphuric acids, or organic acids such as, e.g., citric, tartaric, fumaric or methanesulphonic acid, and salts with bases, either inorganic bases such as, e.g., alkali or alkaline-earth metal hydroxides in particular sodium and potassium hydroxides, or organic bases such as, e.g., triethylamine, pyridine, benzylamine or collidine.

Preferred salts are the salts of the compounds of formula (I) wherein R$_2$ is hydrogen with one of the bases hereabove specified, in particular with sodium hydroxide or potassium hydroxide.

All the possible isomers of formula (I), both geometrical and optical isomers, and their mixtures, may be obtained by the new pocess of the invention. Preferred isomers of formula (I) are those having the 5(R) configuration and when, according to a preferred feature of the invention, R$_1$ is an α-hydroxy substituted ethyl group, the (5R, 6S, 8R) and (5R, 6R, 8S), in particular (5R, 6S, 8R), configurations are the preferred ones.

According to the new process which is the first object of the invention the compounds of formula (I) are prepared by reacting a compound of formula (II)

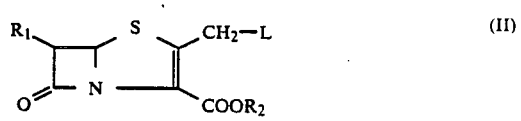

wherein R$_1$ and R$_2$ are as defined above and L is chlorine, bromine or a free or activated hydroxy group, with a compound of formula (III)

wherein Y is as defined above, or a salt thereof, or a reactive derivative thereof, and, if desired, converting an obtained compound of formula (I) into another compound of formula (I) and/or, if desired, salifying a free compound of formula (I) or, if desired, obtaining a free compound of formula (I) from a salt thereof and/or, if desired separating a mixture of isomers of formula (I) into the single isomers.

An activated hydroxy group L in a compound of formula (II) is a hydroxy group activated in the form of a reactive ester or reactive complex or reactive acetal. A reactive derivative of a compound of formula (III) is either a compound of formula (III) wherein Y is —S-Het and wherein the mercapto group of the corresponding compound Het-S-H is in an activated form, or a compound of formula (III) wherein Y is formyloxy or a C$_2$-C$_6$ carboxylic acyloxy and wherein the carboxy group of the corresponding carboxylic acid is in an activated form.

A reactive derivative of a compound of formula (III), as herein before defined, is used only for the reaction with a compound of formula (II) wherein L is a free hydroxy group. For the reaction with a compound of formula (II) wherein L is chlorine or bromine or an activated hydroxy group, the compound of formula (III) is preferably used as such or as a salt.

When the hydroxy group L in the compound of formula (II) is activated in the form of a reactive ester, this may be an ester with a sulphonic acid, e.g. methanesulphonic, p-toluenesulphonic, trifluoromethanesulphonic or p-bromobenzenesulphonic acid; or an ester with a phosphoric acid, e.g. a diaryl phosphoric acid, in particular diphenylphosphoric acid; or an ester with a carboxylic acid, e.g. acetic or acetoacetic acid.

When the hydroxy group L is activated in the form of a reactive complex, this may be, for instance, a phosphorous complex between the compound of formula (II) wherein L is hydroxy and the addition product of a derivative of trivalent phosphorus with a C$_1$-C$_6$-alkyl ester of the azodicarboxylic acid: this addition product may be, for example, an aryl-, e.g. phenyl-, or C$_1$-C$_6$ alkyl-derivative of trivalent phosphorus, triphenylphosphine or tributylphosphine for instance, combined with diethyl azo-dicarboxylate. When the hydroxy group L is activated in the form of a reactive acetal, this may be, for example, the mixed acetal between the compound of formula (II) wherein L is hydroxy, a $C_1$–$C_6$ aliphatic, e.g. neopentylic, alcohol, and dimethylformamide.

Preferably the hydroxy group L in a compound of formula (II) is activated in the form of a reactive ester thereof with a sulphonic acid, e.g. one of those hereabove mentioned, or in the form of a reactive complex with a trivalent phosphorus derivative and a $C_1$–$C_6$ alkyl azo-dicarboxylate, e.g. of the type hereabove mentioned.

A reactive derivative of a compound of formula (III) wherein Y is —S-Het, i.e. a compound of formula Het-S—H, is, preferably, a complex between the corresponding disulfide Het-S—S-Het, wherein the two groups Het are the same, and an aryl- or $C_1$–$C_6$-alkyl-derivative of trivalent phosphorus, e.g. of the kind before specified, in particular, for example, tributylphosphine.

A reactive derivative of a compound of formula (III) wherein Y is formyloxy or $C_2$–$C_6$ carboxylic acyloxy, which is carboxylic acid, may be, for instance, a corresponding halide, in particular chloride or bromide, or the anhydride or a mixed anhydride.

A salt of a compound of formula (III) may be the salt with an inorganic base such as, e.g., an alkali or alkaline-earth metal hydroxide, preferably the sodium or potassium hydroxide, or the salt with an organic base such as, e.g., triethylamine or N,N-diisopropylethylamine.

The reaction between a compound of formula (II) and a compound of formula (III), or a salt thereof, or a reactive derivative thereof, may be performed in a suitable organic solvent which may be, for instance, tetrahydrofuran, dimethylformamide, acetone or a halogenated hydrocarbon such as, e.g. dichloromethane.

The reaction temperature may, preferably, vary between about −40° C. and about +40° C., preferably between −20° C. and +10° C. Sometimes, for instance in the case when a compound of formula (III) is used as such, the presence of a base, such as, for instance, triethylamine or pyridine, may be required.

When, for the reaction with a compound of formula (III) or a salt thereof, a compound of formula (II) is used wherein L is chlorine or bromine or a hydroxy group activated in the form of a reactive ester with a sulphonic or phosphoric acid, of the kind specified above, any compound of formula (I), i.e. with any value of the Y substituent, may be obtained.

When, for the reaction with a compound of formula (III) or a salt thereof, a compound of formula (II) is used wherein L is a hydroxy group activated in the form of a reactive ester with a carboxylic acid as before specified, a compound of formula (I) wherein Y is —S-Het, wherein Het is as defined above may be obtained. When the starting material is a compound of formula (II) wherein the hydroxy group L is activated in the form of a reactive complex or reactive acetal of the kind previously described, a compound of formula (I) wherein Y is —S-Het, wherein Het is as defined above, or Y is optionally substituted $C_1$–$C_{12}$ alkylthio, may be obtained.

As is evident from what reported before, the reaction of a compound of formula (II) wherein L is a free hydroxy group with a reactive derivative of a compound of formula (III) leads, according to the possible values of Y in the compound (III), either to a compound of formula (I) wherein Y is —S-Het, wherein Het is as defined above, or to a compound of formula (I) wherein Y is formyloxy or $C_2$–$C_6$ carboxylic acyloxy.

According to a preferred feature, the new process of the invention is used to prepare compounds of formula (I) wherein Y is an optionally substituted group —S-Het, wherein Het is as defined above, either (a) by reacting a compound of formula (III) wherein Y is —S-Het, or a salt thereof, with a compound of formula (II) wherein L is chlorine or bromine or an activated hydroxy group, preferably a hydroxy group activated in the form of a reactive ester with a sulphonic acid, or in the form of a reactive complex obtained upon reaction with a trivalent organophosphorus compound, preferably triphenylphosphine, and an azo-dicarboxylic acid ester, preferably diethylazodicarboxylate; or (b) by reacting a compound of formula (II) wherein L is a free hydroxy group with a reactive derivative of a compound of formula (III) wherein Y is —S-Het, i.e. a complex between the disulfide thereof and a derivative of trivalent phosphorus, e.g. of the kind previously specified.

When in a compound of formula (II) or in a compound of formula (III) any group in present which may interfere in the displacement reaction of the group L by the substituent Y, such group is protected in a conventional manner before the reaction takes place and, if desired, it is removed at the end of the reaction in a conventional manner too.

Optional conversions of a compound of formula (I) into another compound of formula (I) include, for example, the removal of the protecting groups possibly present, e.g. hydroxy, mercapto, amino and carboxy protecting groups. The removal of the protecting groups may be carried out by known methods such as, for instance, hydrogenolysis, e.g. in the presence of palladium on charcoal as catalyst, or by hydrolysis, either acid hydrolysis, e.g. with acetic acid or oxalic acid, or neutral or basic hydrolysis, or hydrolysis under reductive conditions, for example by the use of Fe/NH$_4$Cl or of Na$_2$S$_2$O$_4$.

The optional salification of a free compound of formula (I), the optional preparation of a free compound of formula (I) from a salt thereof, and the optional separation of a mixture of isomers of formula (I) into the single isomers may be carried out following the known and usual procedures of the organic chemistry.

The compounds of formula (II) wherein L is hydroxy are known compounds or may be prepared by known methods from known compounds; they may be also obtained, for example, according to the method described in our published British patent application No. 80 05476.

A compound of formula (II) wherein L is chlorine or bromine may be obtained, e.g., by reacting a compound of formula (II) wherein L is hydroxy with an appropriate halogenating agent which may be, for example, thionyl chloride, a phosphorous halide, phosphorous tribromide for instance, triphenylphosphine/carbontetrachloride or triphenylphosphine/carbon tetrabromide.

A compound of formula (II) wherein L is an activated hydroxy group may be prepared from a compound of formula (II) wherein L is a free hydroxy group by known and conventional procedures.

Thus, for example, a compound of formula (II) wherein L is a hydroxy group activated in the form of a reactive ester with a sulphonic or carboxylic acid may be obtained by reaction with the appropriate sulphonyl halide, preferably chloride or sulphonic anhydride, or, respectively, with the appropriate carboxylic acyl halide, preferably chloride, or anhydride.

Similarly a compound of formula (II) wherein L is a hydroxy group activated in the form of a reactive ester with a phosphoric acid may be prepared by reacting the corresponding formula (IJ) compound wherein L is hydroxy with an appropriate phosphorus halide, preferably chloride. The hereabove indicated transformations of a compound of formula (II) wherein L is a free hydroxy group into a compound of formula (II) wherein L is a hydroxy group activated in the form of a reactive ester are, preferably, performed in an anhydrous solvent such as for instance, tetrahydrofuran, dimethylformamide or a halogenated hydrocarbon, e.g. dichloromethane, optionally in the presence of a base, preferably an organic base such as, for example, triethylamine, pyridine or lutidine.

A compound of formula (II) wherein L is a hydroxy group activated in the form of a reactive complex or reactive acetal of the kind hereabove specified may be obtained by known standard procedures.

In many instances, the compound of formula (II) containing the activated hydroxy group is not actually isolated but is reacted in situ (that is in the same reaction mixture wherein it is obtained from the corresponding compound of formula (II) wherein L is a free hydroxy group) with the compound of formula (III) or the salt thereof: this usually occurs, for example, when a compound of formula (II) is used wherein the hydroxy group is activated in the form of a reactive complex or reactive acetal of the type described above in this specification.

The compounds of formula (III) are known compounds or may be prepared by known methods from known compounds. A reactive derivative of a compound of formula (III) as defined above may be obtained by known and standard procedure from a free compound of formula (III). Also the said reactive derivative of a compound of formula (III) is not, usually, isolated but is reacted in situ, i.e. in the same reaction mixture wherein it is obtained from the compound (III), with the compound of formula (II) wherein L is a free hydroxy group.

The compounds of formula (II) wherein L is a hydroxy group activated in the form of a reactive ester with a sulphonic acid are included in the scope of the present invention.

A further object of the invention are new compounds of the following formula (Ia)

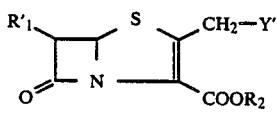

wherein
R'₁ is a $C_1$-$C_6$ alkyl group substituted by a free or protected hydroxy;
R₂ is hydrogen or a carboxy protecting group; and
Y is:
(1) an optionally substituted pyridyl group; or
(2) a group —S—alk—NH₂ wherein alk represents a $C_1$-$C_3$ alkylene; or
(3) a group —S—Het' wherein Het' represents:
(a) 1,3,4-thiadiazolyl either unsubstituted or substituted by a substituent chosen from (a') $C_2$-$C_6$ alkyl; (b') $C_1$-$C_3$ alkyl substituted by an optionally salified carboxy group; (c') an optionally salified carboxymethylthio group; and (d') a group

wherein each of R' and R" is, independently, hydrogen or $C_1$-$C_3$ alkyl;
(b) 1,2,3-thiadiazolyl optionally substituted by a $C_1$-$C_6$ alkyl group;
(c) 1,2,3-triazolyl substituted by a $C_1$-$C_6$ alkyl group;
(d) 1,2,4-triazolyl optionally substituted by a group

wherein R' and R" are as defined above;
(e) 1,3,4-triazolyl optionally substituted by a $C_1$-$C_6$ alkyl group;
(f) imidazolyl optionally substituted by a $C_1$-$C_6$ alkyl group;
(g) thiazolyl optionally substituted by one or more substituents chosen from (a')

wherein R' and R" are as defined above; (b') unsubstituted $C_1$-$C_6$ alkyl; and (c') $C_1$-$C_3$ alkyl substituted by an optionally salified carboxy group;
(h) tetrazolyl optionally substituted by (a') unsubstituted $C_1$-$C_6$ alkyl, or (b') $C_1$-$C_3$ alkyl substituted by a substituent chosen from (i) optionally salified carboxy, (ii) optionally salified sulpho or sulfoamino, (iii) cyano, (iv) carbamoyl, (v)

wherein R' and R" are as defined above, and (vi) tetrazolyl;
(i) pyrazinyl substituted by a $C_1$-$C_6$ alkyl or $C_1$-$C_6$ alkoxy group;
(l) 5-oxo-6-hydroxy-2,5-dihydro-1,2,4-triazinyl and 5-oxo-6-hydroxy-4,5-dihydro-1,2,4-triazinyl both optionally substituted by a $C_1$-$C_3$ alkyl group; or
(m) tetrazolo-pyridazinyl optionally substituted by (a') an optionally salified carboxy group or (b') a group

wherein R' and R" are as defined above; provided that when Y' is a group —S—Het' wherein Het' is 1,2,3,4-tetrazol-5-yl substituted by $C_1$-$C_6$ alkyl at the 1-position, then R'$_1$ is not α-hydroxyisopropyl, and the pharmaceutically or veterinarily acceptable salts thereof.

In the above formula (Ia) a $C_1$-$C_6$ alkyl group is, preferably methyl, ethyl, n-propyl, isopropyl or isobutyl; a $C_2$-$C_6$ alkyl group is, preferably, ethyl or isopropyl; a $C_1$-$C_3$ alkyl group is, preferably, methyl or ethyl; a $C_1$-$C_3$ alkylene is, preferably, ethylene; a $C_1$-$C_6$ alkoxy group is, preferably, methoxy or ethoxy; a group

is, preferably, amino, monomethylamino or dimethylamino; a salified carboxy or sulpho group is, preferably, salified with an alkali metal, sodium in particular, and the protecting groups of the hydroxy and carboxy functions may be the same previously specified with reference to formula (I). Also the pharmaceutically or veterinarily acceptable salts of the compounds of formula (Ia) may be the same indicated above for the compounds of formula (I), and they include both the salts of the compounds of formula (Ia) wherein $R_2$ is hydrogen and the salts of the compounds of formula (Ia) wherein Het' represents a salifiable heterocyclic ring or a heterocyclic ring containing a salifiable substituent, as well as the internal salts, i.e. zwitterions.

Preferred salts are those of the compounds of formula (Ia) wherein $R_2$ is hydrogen with a pharmaceutically or veterinarily acceptable base, particularly an inorganic base such as, e.g., an alkali metal hydroxide, sodium hydroxide or potassium hydroxide for instance.

Preferably in the above formula (Ia) R'$_1$ represents an α-hydroxyethyl, wherein the hydroxy group is either free or protected, for example by a p-nitro-benzyloxycarbonyl or a tert-butyldimethylsilyl group.

Preferably $R_2$ is hydrogen, a cation or a carboxy protecting group chosen from alkyl, p-nitro-benzyl, tert-butyldiphenylsilyl and acetoxymethyl.

When Y' is an optionally substituted pyridyl group it is, preferably, a 1-pyridyl group optionally substituted by a carbamoyl group, in particular 4-carbamoyl.

When Y' is a group —S—alk—NH$_2$ as defined above, it is, preferably, a group —S—CH$_2$—CH$_2$—NH$_2$. When Y' is a group —S—Het', Het' preferably represents:
2-carboxymethyl-1,3,4-thiadiazol-5-yl;
2-amino-1,3,4-thiadiazol-5-yl;
5-carboxymethylthio-1,3,4-thiadiazol-2-yl;
2-amino-1,3-thiazol-5-yl;
4-methyl-5-carboxymethyl-1,3-thiazol-2-yl;
tetrazol-5-yl;
1-methyl-1,2,3,4-tetrazol-5-yl;
1-carboxy-methyl-1,2,3,4-tetrazol-5-yl;
1-carboxy-ethyl-1,2,3,4-tetrazol-5-yl;
1-cyano-methyl-1,2,3,4-tetrazol-5-yl;
1-cyano-ethyl-1,2,3,4-tetrazol-5-yl;
1-sulpho-methyl-1,2,3,4-tetrazol-5-yl;
1-sulpho-ethyl-1,2,3,4-tetrazol-5-yl;
1-dimethylaminomethyl-1,2,3,4-tetrazol-5-yl;
1-dimethylaminoethyl-1,2,3,4-tetrazol-5-yl;
1-aminocarbonylmethyl-1,2,3,4-tetrazol-5-yl;
1-(2-aminocarbonylethyl)-1,2,3,4-tetrazol-5-yl;
6-methoxy-pyrazyn-2-yl;
5-oxo-6-hydroxy-2,5-dihydro-1,2,4-triazin-3-yl;
5-oxo-6-hydroxy-4,5-dihydro-1,2,4-triazin-3-yl;
1,2,3,4-tetrazolo[1,5-b]pyridazin-6-yl;
8-amino-1,2,3,4-tetrazolo[1,5-b]pyridazin-6-yl; or
8-carboxy-1,2,3,4-tetrazolo[1,5-b]pyridazin-6-yl.

Preferred compounds of formula (Ia) are those wherein R'$_1$ is α-hydroxyethyl, with the hydroxy group optionally protected, $R_2$ is hydrogen or a carboxy protecting group and Y' is a group —S—Het' wherein Het' is one of the heterocyclic rings listed hereabove, and the pharmaceutically or veterinarily acceptable salts of these compounds, particularly the sodium and potassium salts.

Other preferred compounds of formula (Ia) are those wherein R'$_1$ and $R_2$ are as hereinbefore defined on this page and Y' is —S—CH$_2$—CH$_2$—NH$_2$, and the pharmaceutically or veterinarily acceptable salts thereof.

All the possible isomers of formula (Ia), both geometrical and optical isomers, and their mixtures, and the metabolites and the metabolic precursors of the compounds of formula (Ia) are included in the scope of the present invention.

Preferred configuration for the compounds of formula (Ia) is the (5R,6S) configuration and when, according to a particularly preferred feature, R'$_1$ is an α-hydroxyethyl group, the (5R,6S,8R) and (5R,6R,8S) configurations are the preferred ones, the (5R,6S,8R) configuration being most preferred.

Specific examples of preferred compounds of the invention are:
(5R,6S)-6-[1(R)-hydroxyethyl]-2-[(1-methyl-1,2,3,4-tetrazol-5-yl)-thiomethyl]-penem-3-carboxylic acid;
(5R,6S)-6-[1(R)-hydroxyethyl]-2-[(2-amino-1,3,4-thiadiazol-5-yl)-thiomethyl]-penem-3-carboxylic acid;
(5R,6S)-6-[1(R)-hydroxyethyl]-2-[(5-carboxy-methylthio-1,3,4-thiadiazol-2-yl)-thiomethyl]-penem-3-carboxylic acid;
(5R,6S)-6-[1(R)-hydroxyethyl]-2-(1,2,3,4-tetrazol-5-yl)-thiomethyl-penem-3-carboxylic acid;
(5R,6S)-6-[1(R)-hydroxyethyl]-2-[1-(2-aminocarbonylethyl)-1,2,3,4-tetrazol-5-yl]-thiomethyl-penem-3-carboxylic acid;
(5R,6S)-6-[1(R)-hydroxyethyl]-2-[1-(2-cyanoethyl)-1,2,3,4-tetrazol-5-yl-thiomethyl-penem-3-carboxylic acid;
(5R,6S)-6-[1(R)-hydroxyethyl]-2-(5-carboxymethyl-1,3,4-thiadiazol-2-yl)-thiomethyl-penem-3-carboxylic acid;
(5R,6S)-6-[1(R)-hydroxyethyl]-2-[1-(2-dimethylaminoethyl)-1,2,3,4-tetrazol-5-yl]-thiomethyl-penem-3-carboxylic acid;
(5R,6S)-6-[1(R)-hydroxyethyl]-2-(1-carboxymethyl-1,2,3,4-tetrazol-5-yl)-thiomethyl-penem-3-carboxylic acid;
(5R,6S)-6-[1(R)-hydroxyethyl]-2-[1-(2-carboxyethyl)-1,2,3,4-tetrazol-5-yl]-thiomethyl-penem-3-carboxylic acid;
(5R,6S)-6-[1(R)-hydroxyethyl]-2-(1-sulphomethyl-1,2,3,4-tetrazol-5-yl)-thiomethyl-penem-3-carboxylic acid;
(5R,6S)-6-[1(R)-hydroxyethyl]-2-(4-carboxymethyl-5-methyl-1,3-thiazol-2-yl)-thiomethyl-penem-3-carboxylic acid;

(5R,6S)-6-[1(R)-hydroxyethyl]-2-(tetrazolo[1,5-b]pyridazin-6-yl)-thiomethyl-penem-3-carboxylic acid;

(5R,6S)-6-[1(R)-hydroxyethyl]-2-(8-carboxytetrazolo[1,5-b]pyridazin-6-yl)-thiomethyl-penem-3-carboxylic acid;

(5R,6S)-6-[1(R)-hydroxyethyl]-2-(8-aminotetrazolo[1,5-b]pyridazin-6-yl)-thiomethyl-penem-3-carboxylic acid;

(5R,6S)-6-[1(R)-hydroxyethyl]-2-(6-methoxy-pyrazin-2yl)-thiomethyl-penem-3-carboxylic acid;

(5R,6S)-6-[1(R)-hydroxethyl]-2-(2-methyl-5-oxo-6-hydroxy-2,5-dihydro-1,2,4-triazin-3-yl)-thiomethyl-penem-3-carboxylic acid;

(5R,6S)-6-[1(R)-hydroxyethyl]-2-(4-methyl-5-oxo-6-hydroxy-4,5-dihydro-1,2,4-triazin-3-yl)-thiomethyl-penem-3-carboxylic acid;

(5R,6S)-6-[1(R)-hydroxyethyl]-2-(2-aminothiazol-5-yl)-thiomethyl-penem-3-carboxylic acid;

and the pharmaceutically or veterinarily acceptable salts thereof, in particular the sodium and potassium salts.

Another example of preferred compounds of the invention is (5R,6S)-6-[1(R)-hydroxyethyl]-2-($\beta$-aminoethyl)-thiomethyl-penem-3-carboxylic acid, and the pharmaceutically or veterinarily acceptable salts thereof.

The compounds of formula (Ia) may be prepared by the new process of the invention, involving the reaction between a compound of formula (II) and a compound of formula (III). The compounds of formula (Ia) may also be prepared by a process comprising cyclizing a compound of formula (IV)

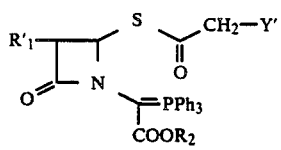

wherein $R_1'$, $R_2$ and $Y'$ are as defined above and Ph is phenyl, and, if desired, converting an obtained compound of formula (Ia) into another and/or, if desired, salifying a free compound of formula (Ia) or obtaining a free compound of formula (Ia) from a salt thereof and-/or, if desired, separating a mixture of isomers of formula (Ia) into the single isomers.

The cyclization of a compound of formula (IV) may be carried out by known conventional procedures, for example by heating in an inert solvent such as, for instance, an aromatic hydrocarbon like benzene or toluene, at temperatures varying from about 50° C. to about 140° C., as reported, e.g. in our published British patent application No. 80 05476, published G.B. No. 2043639, Oct. 8, 1980. The optional conversion of a compound of formula (Ia) into another, such as, for example, the removal of possibly present protecting groups, the optional salification of a compound of formula (Ia) and the preparation of a free compound from a salt, as well as the optional separation of a mixture of isomers into the single isomers, may be carried out as reported above for the analogous transformations on the compounds of formula (I).

The compounds of formula (IV) may be prepared following known methods, e.g. as described in our published British patent application No. 80 05476.

The compounds of formula (I) and (Ia) have a high antibacterial activity both in animals and in humans against gram-positive and gram-negative bacteria such as staphylococci, streptococci, diplococci, Klebsiella, *Escherichia coli, Proteus mirabilis,* Salmonella, Shigella, Haemophilus and Neisseria. They show also a high activity against the strong beta-lactamase producer microorganisms, such as, for example, *Klebsiella aerogenes* 1082 E, *Escherichia coli* TEM, *Enterobacter cloacae* P 99, and indole-positive Proteus and the like, as well as against *Pseudomonas aeruginosa* strains.

For example, the compound (5R,6S)-6-[1(R)-hydroxyethyl]-2-{tetrazolo[1,5-b]pyridazin-6-yl}-thiomethyl-penem-3-carboxylic acid was found to be particularly active against Gram-positive bacteria: in particular, for instance, minimal inhibiting concentrations of 0.002 µg/ml against *Streptococcus pyogenes* and pneumoniae and of 0.004 µg/ml against penicillinase producer and non-producer *Staphylococcus aureus* were found for the sodium salt of said compound. For the compound (5R,6S)-6-[1(R)-hydroxyethyl]-2-(2-methyl-5-oxo-6-hyroxy-2,5-dihydro-1,2,4-triazin-3yl)-thiomethyl-penem-3-carboxylic acid disodium salt, for example, a particularly favourable acitivity was found against the Gram-negative bacteria such as, for instance, *Escherichia coli* 1507 E, *Escherichia coli* TEM, *Klebsiella pneumoniae* ATCC 10031 and *Proteus vulgaris* X 20.

Other examples of compounds for which particularly favourable values of minimal inhibiting concentrations were found both against Gram-positive and against Gram-negative bacteria are (5R,6S)-6-[1(R)-hydroxyethyl]-2-[1-(2-aminocarbonylethyl)-1,2,3,4-tetrazol-5-yl]-thiomethyl-penem-3-carboxylic acid, (5R,6S)-6-[1(R)-hydroxyethyl]-2-(5-carboxymethylthio-1,3,4-thiadiazol-2-yl)-thiomethyl-penem-3-carboxylic acid and (5R,6S)-6-[1(R)-hydroxyethyl]-2-[1-methyl-1,2,3,4-tetrazol-5-yl)-thiomethyl]-penem-3-carboxylic acid.

Owing to their high antibacterial activity either in animals or in humans against both Gram-positive and Gram-negative bacteria the compounds of the present invention are useful in the treatment of the infections caused by said microorganisms, such as, respiratory tract infections, for example, bronchitis, bronchopneumonia, pleurisy; hepatobiliary and abdominal infections, for example, septicemia; urinary tract infections, for example, pyelonephritis, cystitis; obstetrical and gynecological infections, for instance, cervicitis, endometritis; ear, nose and throat infections, for instance, otitis, sinusitis, parotitis.

The toxicity of the compounds of the invention is quite negligible and therefore they can be safely used in therapy.

They may be administered, either to humans or to animals, in a variety of dosage forms, e.g., orally in the form of tablets, capsules, drops or syrups; rectally in the form of suppositories; parenterally, e.g., intravenously or intramuscolarly (as solutions or suspensions), with intravenous administration being preferred in emergency situation; by inhalation in the form of aerosols or solutions for nebulizers; intravaginally in the form, e.g., of bougies; or topically in the form of lotions, creams and ointments. The pharmaceutical or veterinary compositions containing the compounds of the invention may be prepared in a conventional way by employing the conventional carriers or diluents used for, e.g., cephalosporins.

Conventional carriers or diluents are, for example, water, gelatine, lactose, starches, magnesium stearate, talc, vegetable oils, cellulose and the like. Daily doses in the range of about 1 to 100 mg per kg of body weight may be used, in various animal species, the exact dose depending on the age, weight and condition of the subject to be treated and on the frequency and route of administration.

A preferred way of administration of the compounds of the invention is the parenteral one: in this case the compounds may be administered, for example to adult humans, in an amount ranging from about 100 mg to about 200 mg pro dose, preferably about 150 mg pro dose, 1–4 times a day, dissolved in a suitable solvent, such as, for example, sterile water or lidocaine hydrochloride solution for intramuscolar injections, and sterile water, physiological saline solution, dextrose solution or the conventional intravenous fluids or electrolytes, for intravenous injections. Furthermore, the compounds of the invention may be used as antibacterial agents in a prophylactic manner, e.g., in cleaning or as surface disinfecting compositions, for example, at a concentration of about 0.2 to 1% by weight of such compounds admixed with, suspended or dissolved in conventional inert dry or aqueous carriers for application by washing or spraying. They are also useful as nutritional supplements in animal feeds.

The abbreviations pNB, THF, EtOAc, TBDMS and TBDPS stand, respectively, for p-nitro-benzyl, tetrahydrofuran, ethylacetate, tert-butyldimethylsilyl and tert-butyldiphenylsilyl.

EXAMPLE 1 p-Nitrobenzyl(5R,6S)-6-[1(R)-hydroxyethyl]-2-nitrobenzyloxycarbonyloxymethyl-2-penem-3-carboxylate

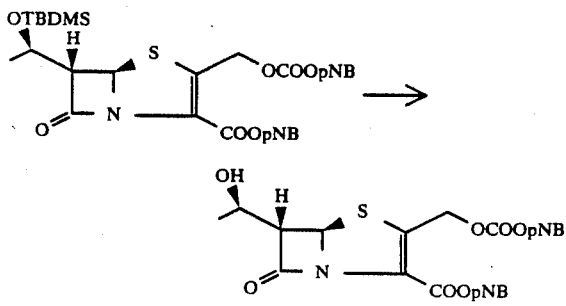

To a solution of p-nitrobenzyl(5R,6S)-6-[1(R)-tert-butyldimethylsilyloxyethyl]-2-p-nitrobenzyloxycarbonyloxymethyl-2-penem-3-carboxylate (950 mg, 1.41 mmol) in THF, acetic acid (806 μl, 14.1 mmol) and tetrabutylammonium fluoride trihydrate (1.33 g, 4.33 mmol) were added at 0° C. with stirring.

The resulting solution was stirred for 22 hours at room temperature.

The organic solvent was removed under reduced pressure. The residue was dissolved in ethyl acetate, washed with 4% aqueous sodium bicarbonate, twice with brine, then dried over $Na_2SO_4$ and concentrated under reduced pressure. The residue was triturated in cyclohexane to give, after filtration of the solvent, white cristals (680 mg, 86%) of the title product.

UV (CHCl$_3$) $\lambda_{max}$ 325 nm.

NMR (CDCl$_3$) δ ppm 1.37 (3H, d, J=6.0 Hz), 2.96 (1H, b.s., exch. with D$_2$O), 3.92 (1H, dd, J=2.0 and 6.0 Hz), 4.26 (1H, m), 5.30 (2H, s), 5.35 (2H, ABq, J=14 Hz, separation of inner lines=14 Hz), 5.42 (2H, ABq, J=13 Hz, separation of inner lines=18 Hz), 5.68 (1H, d, J=2.0 Hz), 7.56 (2H, d, J=7.5 Hz), 7.61 (2H, d, J=7.5 Hz), 8.20 (2H, d, J=7.5 Hz), 8.23 (2H, d, J=7.5 Hz).

EXAMPLE 2

(5R,6S)-6-[1(R)-hydroxymethyl]-2-hydroxymethyl-penem-3-carboxylic acid, sodium salt

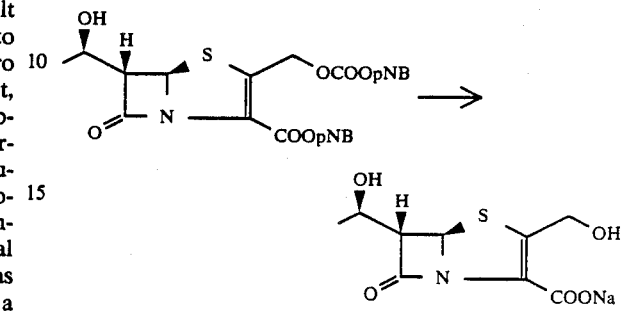

To a solution of p-nitrobenzyl(5R,6S)-6-[1(R)-hydroxyethyl]-2-(p-nitrobenzyloxycarbonyloxymethyl)-penem-3-carboxylate (750 mg, 1.34 mmol) in a mixture of ETOAc (25 ml) and water (25 ml), solid NaHCO$_3$ (112 mg, 1.34 mmol) and 5% Pd/C (750 mg) were added. The two-phase mixture was hydrogenated under normal pressure for 1 hour. A further amount of 5% Pd/C (750 mg) was then added and the hydrogenation was continued for 1 hour. The mixture was then filtrated and the organic phase was discarded. The aqueous phase was concentrated in vacuo to give a brownish oil which was purified on a reverse phase column eluting with water. The title product was so obtained as an amorphous solid (210 mg, 61.2%).

UV (H$_2$O) $\lambda_{max}$ 259, 306 nm.

NMR (D$_2$O) δ ppm 1.30 (3H, d, J=7 Hz), 3.88 (1H, dd, J=1 and 6.3 Hz), 4.23 (1H, m), 4.63 (2H, ABq, J=14.5 Hz, separation of inner lines=4 Hz), 5.62 (1H, d, J=1 Hz).

EXAMPLE 3

(5R,6S)-6-[1(R)-tert-butyldimethylsilyloxyethyl]-2-hydroxymethyl-2-penem-3-carboxylic acid

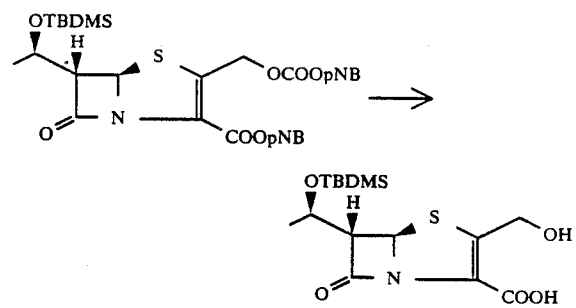

A solution of sodium bicarbonate (110 mg, 1.3 mmol) in water (25 ml) was added to a solution of p-nitrobenzyl(5R,6S)-6-[1-(R)-tert-butyldimethylsilyloxyethyl]-2-p-nitrobenzyloxycarbonyloxymethyl-penem-3-carboxylate (875 mg, 1.3 mmol) in ethyl acetate (25 ml). The mixture was hydrogenated over 5% palladium on charcoal catalyst (875 mg) for 2 hours.

A further amount of 5% palladium on charcoal (875 mg) was added and the mixture hydrogenated for four hours. After filtration through Hiflo filter aid, the aqueous phase was separated, concentrated in vacuo and the resulting residue was purified on a reverse phase column giving the sodium salt of the title compound as a white solid (252 mg, 52%).

An aqueous solution of the sodium salt was acidified with acetic acid and extracted with ethyl acetate. The organic solvent was dried over sodium sulphate and evaporated under reduced pressure to give the free carboxylic acid as a light yellow foam.

UV (CHCl$_3$) $\lambda_{max}$ 324 nm.

IR (CHCl$_3$) $\nu_{max}$ 1785, 1710 cm$^{-1}$.

NMR (CDCl$_3$) $\delta$ ppm 0.06 (3H, s), 0.90 (9H, s), 1.26 (3H, d, J=6.0 Hz), 3.73 (1H, dd, J=1.5, 5 Hz), 4.22 (1H, m), 4.67 (2H, s), 5.59 (1H, d, J=1.5 Hz).

EXAMPLE 4 p-Nitrobenzyl-(5R,6S)-6-[1(R)-tert-butyldimethylsilyloxyethyl]-2-hydroxymethyl-penem-3-carboxylate

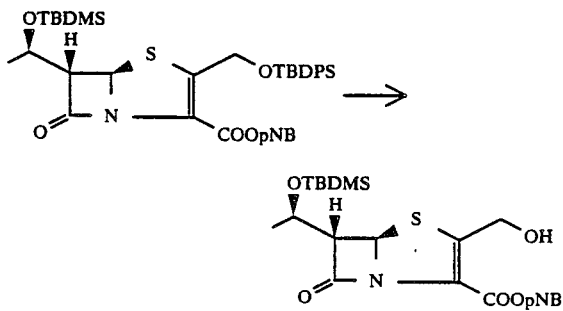

A solution of p-nitrobenzyl(5R,6S)-6-[1(R)-tert-butyldimethylsilyloxyethyl]-2-tert-butyldiphenyl-silyloxymethyl-penem-3-carboxylate (0.73 g, 1 mmol) in tetrahydrofuran (20 ml) was sequentially treated at +10° C. with acetic acid (0.7 ml, 10 mmol) and tetrabutylammonium fluoride trihydrate (0.95 g, 3 mmol), and the mixture stirred at the same temperature until most of the starting material had disappeared (TLC, ~3 h).

The solvent was removed under vacuum and the residue was partitioned between ethyl acetate and aqueous sodium hydrogen carbonate. Evaporation of the organic phase, followed by cromatographic purification (SiO$_2$, ethyl acetate-cyclohexane mixtures as eluants) affored the title compound (345 mg, 70%) as a white foam.

NMR (CDCl$_3$) $\delta$ ppm 0.05 (6H, s), 0.85 (9H, s), 1.25 (3H, d), 3.44 (1H, t, exch. with D$_2$O), 3.78 (1H, dd), 4.29 (1H, m), 4.64 (2H, d, collapses to a s after exch. with D$_2$O), 5.32 (2H, ABq), 5.64 (1H, d), 7.60 (2H, d), 8.20 (2H, d).

EXAMPLE 5 p-Nitrobenzyl(5R,6S)-6-[1(R)-hydroxyethyl]-2-hydroxymethyl-penem-3-carboxylate

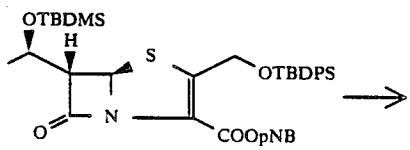

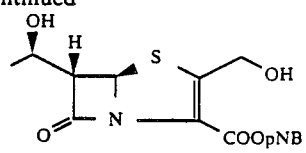

A solution of p-nitrobenzyl(5R,6S)-6-[1(R)-tert-butyldimethylsilyloxyethyl]-2-tert-butyldiphenyl-silyloxymethyl-penem-3-carboxylate (0.93 g, 1 mmol) in tetrahydrofuran (20 ml) was stirred for 20 h at room temperature in the presence of acetic acid (1.14 ml, 20 mmol) and tetrabutylammonium fluoride trihydrate (1.89 g, 6 mmol). The solvent was removed in vacuo and the residue was partitioned between ethyl acetate and an aqueous solution of sodium hydrogen carbonate. The organic layer was washed with water, dried over Na$_2$SO$_4$ and evaporated to give a syrup which was purified by trituration in a small amount of dichloromethane. The title product was collected as a white-off powder (290 mg; 76%).

UV (EtOH) $\lambda_{max}$ 264, 322 nm.

IR $\nu_{max}$ 3400-3200, 1780, 1690 cm$^{-1}$.

NMR (EtOH-d$_6$) $\delta$ ppm 1.45 (3H, d, J=6.5 Hz), 3.67 (1H, dd, J=1.5, 6.0 Hz), 4.10 (1H, m), 4.72 (2H, s), 5.32 (2H, ABq, J=14 Hz), 5.59 (1H, d, J=1.5 Hz), 7.69 (2H, d, J=7 Hz), 8.18 (2H, d, J=7 Hz).

EXAMPLE 6 p-Nitrobenzyl(5R,6S)-6-[1(R)-p-nitrobenzyloxycarbonyloxyethyl]-2-hydroxymethyl-penem-3-carboxylate

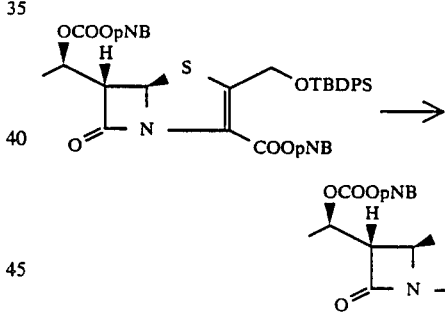

Acetic acid (157 $\mu$l; 2.76 mmol) and tetrabutylammonium fluoride trihydrate (261 mg, 0.827 mmol) were sequentially added to a solution of p-nitrobenzyl(5R,6S)-6-[1(R)-p-nitrobenzyloxycarbonyloxyethyl]-2-tert-butyldiphenylsilyloxymethyl-penem-3-carboxylate (220 mg, 0.276 mmol) in tetrahydrofuran (10 ml) and the mixture was stirred for several hours at room temperature.

Work-up after 4-5 hours, as described in Example 1, afforded the title product as the major component. Silica gel chromatography (EtOAc-cyclohexane mixtures) gave the pure material.

$[\alpha]_D^{20} + 66°$ (1.3% in CHCl$_3$).

UV (CH$_2$Cl$_2$) $\lambda_{max}$ 269 ($\epsilon$=17.000) and 323 ($\epsilon$=6.800) nm.

IR (CH$_2$Cl$_2$) $\nu_{max}$ 1795, 1755 and 1710 cm$^{-1}$.

NMR (CDCl$_3$) $\delta$ ppm 1.51 (3H, d, J=6.5 Hz), 3.55 (1H, bs), 3.97 (1H, dd, J=2.0 and 8.0 Hz), 4.68 (2H, s), 5.19 (1H, dq, J=6.5 and 8.0 Hz), 5.25-5.45 (4H, m), 5.65 (1H, d, J=2.0 Hz), 7.4-8.5 (8H, m).

When the reaction was left running for a prolonged time (15 hours or more), an elimination product (E, Z mixture) was collected as the major component:

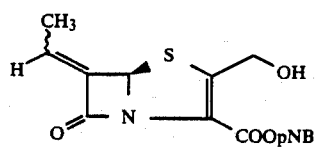

IR (nujol) $\lambda_{max}$ 3550–3100, 1800, 1785–1760, 1705 and 1685 cm$^{-1}$.

NMR (CDCl$_3$) δ ppm (Z)isomer: 1.95 (3H, t, J=8.0 Hz), 4.65 (2H, s), 5.32 (2H, ABq, J=14 Hz), separation of inner lines 6 Hz), 6.13 (1H, s), 6.46 (1H, q), (E)isomer: 2.15 (3H, t, J=7.5 Hz), 4.65 (2H, s), 5.32 (2H, ABq, J=14 Hz), separation of inner lines 6 Hz), 6.13 (1H, s), 6.20 (1H, dq).

EXAMPLE 7 p-Nitrobenzyl(5R,6S)-6-[1(R)-hydroxyethyl]-2-hydroxymethyl-penem-3-carboxylate

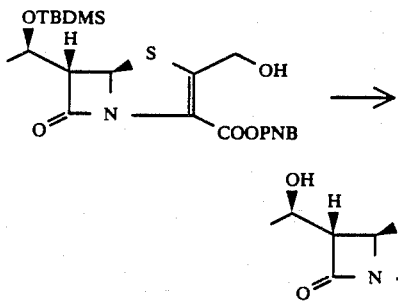

To a solution of p-nitrobenzyl(5R,6S)-2-hydroxymethyl-6-[1(R)-tert-butyldimethylsilyloxyethyl]-penem-3-carboxylate (1.2 g, 2.4 mmol) in THF (50 ml) acetic acid (1.47 ml, 24 mmol) and tetrabutylammonium fluoride (2.27 g, 7.2 mmol) were added.

The resulting mixture was stirred at room temperature for 16 hours.

The solution was then evaporated in vacuo and the residue was chromatographed on silica gel eluting with ethyl acetate/cyclohexane mixtures to give the title product as a light yellow solid (775 mg, 85%).

UV (EtOH) $\lambda_{max}$ 264, 322.

NMR (EtOH-d$_6$) δ ppm 1.45 (3H, d, J=6.5 Hz), 3.67 (1H, dd, J=1.5, 6.0 Hz), 4.10 (1H, m), 4.72 (2H, s), 5.32 (2H, ABq, J=14 Hz, separation of inner lines 8 Hz), 5.59 (1H, d, J=1.5 Hz), 7.69 (2H, d, J=7 Hz), 8.18 (2H, d, J=7 Hz).

EXAMPLE 8

Sodium(5R,6S)-6-[1(R)-hydroxyethyl]-2-hydroxymethyl-penem-3-carboxylate

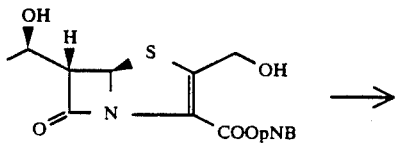

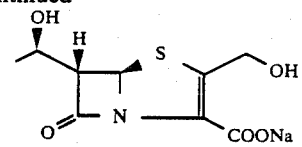

A solution of p-nitrobenzyl(5,6S)-6-[1(R)-hydroxyethyl]-2-hydroxymethyl-penem-3-carboxylate (450 mg, 1.2 mmol) in EtOAc (25 ml) and water (25 ml) containing NaHCO$_3$ (100 mg, 1.2 mmol) was hydrogenated over 5% Pd/C (450 mg). The reaction was then carried out as described in Example 2. The title product was obtained as an amorphous solid (250 mg, 81%).

The product proved to be identical with the one obtained in Example 2.

EXAMPLE 9

Sodium(5R,6S)-6-[1(R)-hydroxyethyl]-2-hydroxymethyl-penem-3-carboxylate

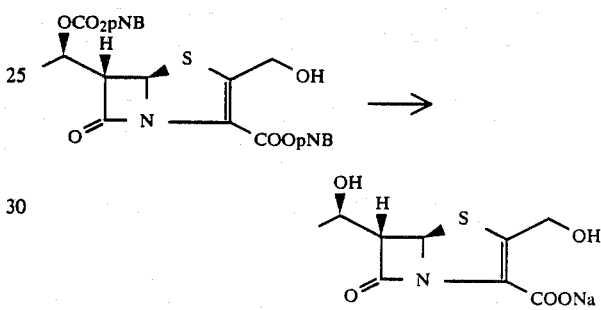

A solution of p-nitrobenzyl(5R,6S)-6-[1(R)-p-nitrobenzyloxycarbonyloxyethyl]-penem-3-carboxylate (950 mg, 0.17 mmol) in EtOAc (25 ml) was hydrogenated as described in Example 2, thus obtaining the title compound as a solid (230 mg, 51.3%).

This material proved to be identical with the compound obtained in Example 2.

EXAMPLE 10

Diphenyl-tert-butylsilyl(5R,6S)-6-[1(R)-hydroxyethyl]-2-hydroxymethyl-penem-3-carboxylate

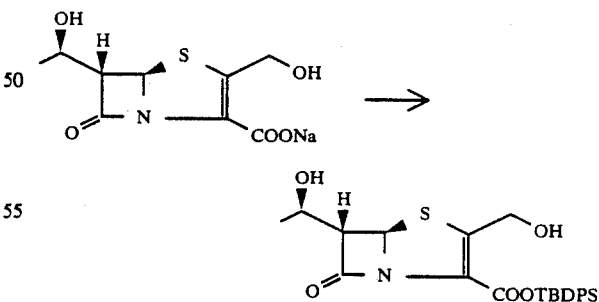

A suspension of sodium(5R,6S)-6-[1(R)-hydroxyethyl]-2-hydroxymethyl-penem-3-carboxylate (108 mg, 0.4 mmol) in anhydrous THF (20 ml) was treated with tert-butyldiphenylsilylchloride (104 μl, 0.4 mmol).

The heterogeneous mixture was stirred for 2 hours at room temperature. The suspension was then filtered and the filtrate was evaporated in vacuo to give an oil which was purified on a silica gel column eluting with EtOAc/cyclohexane mixtures.

The title product was thus obtained as a colourless oil (150 mg, 77.4%).

UV (CHCl₃) λ$_{max}$ 328 nm.

NMR (CDCl₃) δ ppm 1.11 (9H, s), 1.32 (3H, d, J=6 Hz), 3.76 (1H, dd, J=1.5, 6.0 Hz), 4.17 (1H, m), 4.53 (2H, s), 5.58 (1H, d, J=1.5 Hz), 7.22–7.90 (10H, m).

EXAMPLE 11

Tert-butyldiphenylsilyl(5R,6S)-6-[1(R)-hydroxyethyl]-2-methanesulphonyloxymethyl-penem-3-carboxylate

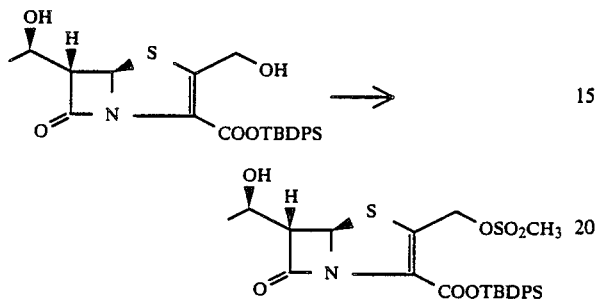

Triethylamine (45 ul, 0.32 mmol) and methanesulphonyl chloride (25 μl, 0.32 mmol) were sequentially added to a stirred solution of diphenyl-tert-butylsilyl(5R,6S)-6-[1(R)-hydroxyethyl]-2-hydroxymethyl-penem-3-carboxylate (150 mg, 0.31 mmol) in cold (−30° C.), anhydrous dichloromethane (5 ml). The progress of the reaction was monitored by TLC.

The reaction mixture was then washed with aqueous NaHCO₃ solution and water. The organic phase was separated, dried over anhydrous Na₂SO₄, and evaporated in vacuo at a temperature below 10° C. The title product was thus obtained an an oil (150 mg, 86%).

UV (CHCl₃) λ$_{max}$ 329 nm.

NMR (CDCl₃) δ ppm 1.10 (9H, s), 1.34 (3H, d, J=6.5 Hz), 3.10 (3H, s), 3.81 (1H, dd, J=1.5, 6.0 Hz), 4.21 (1H, m), 5.17 (2H, Abq, J=12 Hz, separation of inner lines 16 Hz), 5.66 (1H, d, J=1.5 Hz), 7.21–7.85 (10H, m).

EXAMPLE 12

Tert-butyldiphenylsilyl(5R,6S)-6-[1(R)-hydroxyethyl]-2-[(1-methyl-1,2,3,4-tetrazol-5-yl)-thiomethyl]-penem-3-carboxylate

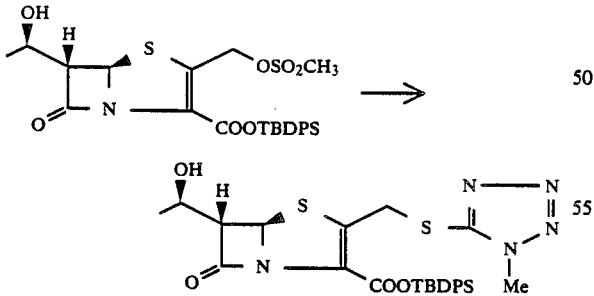

To a solution of tert-butyldiphenylsilyl(5R,6S)-6-[1(R)-hydroxyethyl]-2-methanesulphonyloxymethyl-penem-3-carboxylate (150 mg, 0.27 mmol) in EtOAc (2 ml) a solution of 1-methyl-5-mercapto-1,2,3,4-tetrazole sodium salt (41.5 mg, 0.3 mmol) in anhydrous THF (5 ml) was added at −30° C. with stirring.

The resulting mixture was let stand at −30° C. for 6 hours and then was evaporated in vacuo. The residue was taken up in EtOAc (5 ml) and carefully washed with aqueous NaHCO₃ and water. The organic layer was dried over anhydrous Na₂SO₄ and evaporated in vacuo to give the title product as an oil (97 mg, 62%).

UV (CHCl₃) λ$_{max}$ 337 nm.

NMR (CDCl₃) δ ppm 1.13 (9H, s), 1.34 (3H, d, J=6.0 Hz), 3.82 (1H, dd, J=2.0, 6.0 Hz), 3.85 (3H, s), 4.19 (1H, m), 4.6 (2H, ABq, J=14 Hz, separation of inner lines=17 Hz), 5.61 (1H, d, J=1.5 Hz), 7.24–7.83 (10H, m).

EXAMPLE 13

Sodium(5R,6S)-6-[1(R)-hydroxyethyl]-2-[(1-methyl-1,2,3,4-tetrazol-5-yl)-thiomethyl]-penem-3-carboxylate

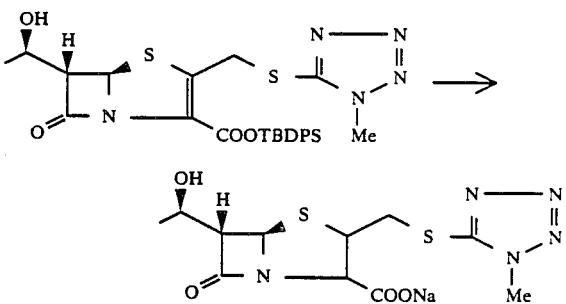

A solution of tert-butyldiphenylsilyl(5R,6S)-6-[1(R)-hydroxyethyl]-2-[(1-methyl-1,2,3,4-tetrazol-5-yl)-thiomethyl]-penem-3-carboxylate (95 mg, 0.14 mmol) in THF (2 ml), H₂O (2 ml) and acetic acid (1 ml) was stirred at room temperature for 2 hours. The solution was then evaporated in vacuo at a temperature below 10° C. The oily residue was taken up in 2% aqueous NaHCO₃ (1 ml). The aqueous phase was washed with EtOAc and the organic phase was discarded. The aqueous phase was then passed through a reverse phase column. Elution with water yielded the title product as an amorphous solid (34 mg, 67%).

UV (H₂O) λ$_{max}$ 315 nm.

NMR (D₂O) δ ppm 1.28 (3H, d, J=6.3 Hz), 3.87 (1H, dd, J=1.4 and 6.3 Hz), 4.10 (3H, s), 4.19 (1H, m), 4.40 (2H, ABq, J=16.0 Hz, separation of inner lines=13 Hz), 5.59 (1H, d, J=1.4 Hz).

EXAMPLE 14

Sodium(5R,6S)-6-[1(R)-hydroxyethyl]-2-[(1-methyl-1,2,3,4-tetrazol-5-yl)-thiomethyl]-penem-3-carboxylate

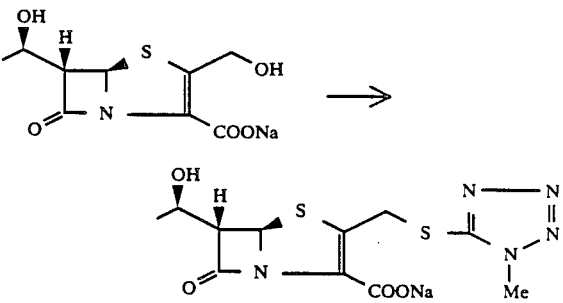

Method A

A suspension of sodium(5R,6S)-6-[1(R)-hydroxyethyl]-2-hydroxymethyl-penem-3-carboxylate (100 mg, 0.37 mmol) in anhydrous THF (20 ml) was treated with tert-butyldiphenylsilyl chloride (96 μl, 0.37 mmol). The heterogeneous mixture was stirred for 2 hours at room temperature.

The suspension was filtered and the filtrate was cooled at −30° C. Et₃N (52 μl, 0.37 mmol) and methanesulphonyl chloride (29 μl, 0.37 mmol) were then added dropwise to this solution under stirring. After 30 minutes, the resulting mixture was partitioned between EtOAc and an aqueous NaHCO₃ solution.

The organic phase was carefully washed with water, dried over anhydrous Na₂SO₄, filtered and cooled again at −30° C. A solution of 1-methyl-5-mercapto-1,2,3,4-tetrazole sodium salt (55.2 mg, 0.4 mmol) in THF (10 ml) was then added. After 6 hours at −30° C. the mixture was evaporated in vacuo and the residue was taken up in EtOAc and washed with water.

The dried organic phase was evaporated in vacuo and the oily residue dissolved in THF (2 ml). Acetic acid (1 ml) and water (2 ml) were added, the solution was stirred at room temperature for 2 hours and then evaporated in vacuo. The oily residue was taken up with 2% aqueous NaHCO₃, washed with FtOAc and purified through a reverse phase column to give the title product, identical with the one described in Example 13.

Method B

A suspension of sodium(5R,6S)-6-[1(R)-hydroxyethyl]-2-hydroxymethyl-penem-3-carboxylate (100 mg, 0.37 mmol) in anhydrous THF was treated with trimethylsilyl chloride (150 μl, 0.4 mmol). The heterogeneous mixture was stirred for 2 hours at room temperature. The suspension was then filtered and the filtrate was cooled at −30° C. Et₃N (52 μl, 0.37 mmol) and methanesulphonyl chloride (29 μl, 0.37 mmol) were then added to the solution drop by drop with stirring, followed after half an hour by a THF solution of 1-methyl-5-mercapto-1,2,3,4-tetrazole sodium salt (55.2 mg, 0.4 mmol).

The resulting mixture was stirred at −30° C. for 6 hours, after which time was evaporated in vacuo to dryness. The residue was dissolved in water containing NaHCO₃ and the solution was passed through a reverse phase column to yield the title product, which was found identical with the one obtained by the above method A.

EXAMPLE 15 p-Nitrobenzyl(5R,6S)-6-[1(R)-p-nitrobenzyloxycarbonyloxyethyl]-2-methylsulphonyloxymethyl-penem-3-carboxylate

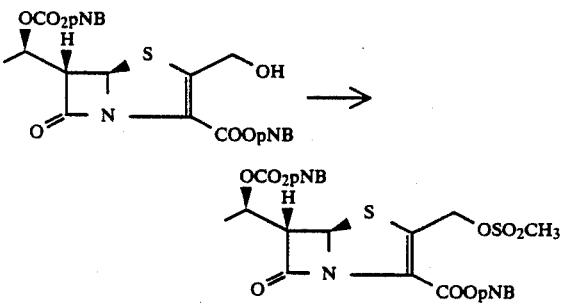

A solution of p-nitrobenzyl(5R,6S)-6-[1(R)-p-nitrobenzyloxycarbonyloxyethyl]-2-hydroxymethyl-2-penem-3-carboxylate (100 mg, 0.178 mmol) in gry dichloromethane (5 ml) was sequentially treated at −15° C. with triethylamine (58 mg, 0.58 mmol) and methanesulphonylchloride (60 mg, 0.58 mmol). After 10 minutes the reaction mixture was washed with aqueous sodium bicarbonate and then with water. The dried (Na₂SO₄) organic phase was evaporated in vacuo to give the title product as a pale yellow syrup.

UV (CHCl₃) λ$_{max}$ 266, 325 nm.

NMR (CDCl₃) δ ppm 1.51 (3H, d, J=7 Hz), 3.09 (3H, s), 4.02 (1H, dd, J=2 and 7.5 Hz), 4.92 and 5.64 (2H, centres of ABq, J=17 Hz), 5.16 (1H, m), 5.25 (2H, s), 5.27 and 5.51 (2H, centres of ABq, J=15 Hz), 5.71 (1H, d, J=2 Hz), 7.50 (2H, d, J=8 Hz), 7.60 (2H, d, J=8 Hz), 8.20 (4H, two superimposing d, J=8 Hz).

MS (FD) m/e 637 (M⁺). C₂₅H₂₃N₃O₁₃S₂ requires M, 637.

EXAMPLE 16 p-Nitrobenzyl(5R,6S)-6-[1(R)-p-nitrobenzyloxycarbonyloxyethyl]-2-[1-methyl-1,2,3,4-tetrazol-5-yl-thiomethyl]-penem-3-carboxylate

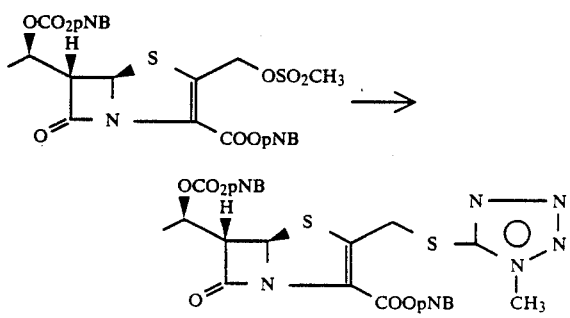

1-methyl-5-mercapto-tetrazole sodium salt bihydrate (52 mg, 0.3 mmol) was added in a single portion to a cold THF solution (20 ml) of the mesylate obtained in Example 15 (38 mg, 0.06 mmol).

After one hour at 0° C. the reaction mixture was evaporated, and the residue chromatographed on silica gel eluting with cyclohexane/EtOAc mixture. The title product was thus obtained as a pale yellow syrup (29 mg, 75%).

UV (CHCl₃) λ$_{max}$ 266 and 330 nm

NMR (CDCl₃) δ ppm 1.48 (3H, d, J=7 Hz), 3.84 (1H, dd, J=2 and 5.5 Hz), 3.96 (3H, s), 4.69 (2H, ABq, J=14 Hz, separation of inner lines 18 Hz), 5.20 (1H, m), 5.24 (2H, s), 5.27 (2H, ABq, J=13 Hz, separation of inner lines 20 Hz), 5.61 (1H, d, J=2 Hz), 7.51 (2H, d, J=8 Hz), 7.82 (2H, d, J=8 Hz), 8.02 (4H, two superimposing d, J=8 Hz).

MS (FD) m/e 657 (M⁺). C₂₆H₂₃N₇O₁₀S₂ requires M, 657.

EXAMPLE 17 p-Nitrobenzyl(5R,6S)-6-[1(R)-p-nitrobenzyloxycarbonyloxy-ethyl]-2-p-tolyl sulphonyloxymethyl-penem-3-carboxylate

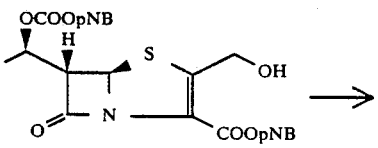

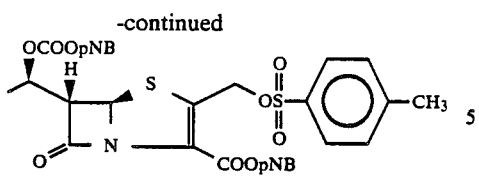

To a stirred solution of p-nitrobenzyl(5R,6S)-6-[1(R)-p-nitrobenzyloxycarbonyloxyethyl]-2-hydroxymethyl-penem-3-carboxylate (56 mg, 100 μmol) in dichloromethane (2 ml) at 0° C., triethylamine (17 μl, 120 μmol) nd p-toluenesulphonyl chloride (21 mg, 110 μmol) were sequentially added. The resulting solution was stirred at 0° C. for 15 minutes. A further amount of triethylamine (10 μl) and p-toluenesulphonyl chloride (13 mg) was added and the mixture was stirred for twenty minutes at 5° C.

After this time the organic solution was washed with a 4% aqueous sodium bicarbonate solution, then with brine. The organic phase was dried over $Na_2SO_4$ and concentrated in vacuo.

Chromatography of the residue on silica gel (elution with hexane/ethyl acetate mixtures) gave a light yellow oil (42 mg, 79%).

UV (CHCl$_3$) $\lambda_{max}$ 267, 327 nm.

IR (film) $\nu_{max}$ 1795, 1750, 1710 cm$^{-1}$.

NMR (CDCl$_3$) δ ppm 1.50 (3H, d, J=6.0 Hz), 2.47 (3H, s), 3.82 (1H, dd, J=2.0, 6.0 Hz), 5.00–5.55 (4H, 2ABq), 5.19 (1H, m), 5.31 (2H, s), 5.63 (1H, d, J=2 Hz), 7.27–7.82 (8H, m), 8.22 (4H, d, J=8 Hz).

EXAMPLE 18 p-Nitrobenzyl(5R,6S)-6-[1(R)-p-nitrobenzyloxycarbonyloxyethyl]-2-(1-methyl-1,2,3,4-tetrazol-5-yl)-thiomethyl-penem-3-carboxylate

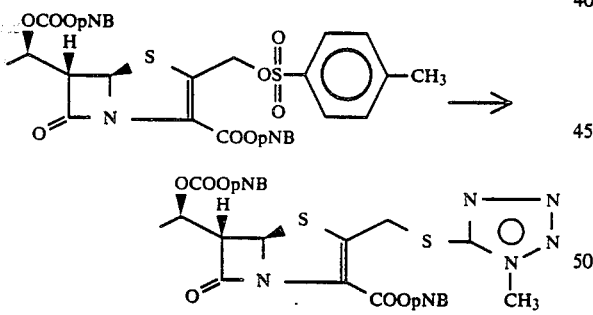

A solution of p-nitrobenzyl(5R,6S)-6-[1(R)-p-nitrobenzyloxycarbonyloxyethyl]-2-p-tolylsulphonyloxymethyl-penem-3-carboxylate (42 mg, 0.059 mmol) in tetrahydrofuran was treated with 1-methyl-5-mercapto-1,2,3,4-tetrazole sodium salt bihydrate (52 mg, 0.3 mmol). The mixture was stirred for 3 hours at room temperature, the solvent was concentrated under vacuum and the residue pertitioned between EtOAc and aqueous NaHCO$_3$.

The organic phase was dried (Na$_2$SO$_4$) and evaporated to give a crude which was purified through a silica gel column (EtOAc/C$_6$H$_{12}$), thus affording 26 mg (68%) of the title product, identical in every respect with the sample described in Example 16.

EXAMPLE 19 p-Nitrobenzyl(5R,6S)-6-[1(R)-p-nitrobenzyloxycarbonyloxyethyl]-2-chloromethyl-penem-3-carboxylate

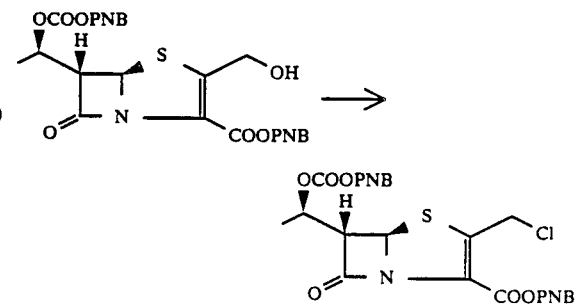

To a solution of p-nitrobenzyl(5R,6S)-6-[1(R)-p-nitrobenzyloxycarbonyloxyethyl]-2-hydroxymethyl-penem-3-carboxylate (210 mg, 0.376 mmol) in methylene chloride (6 ml) and carbon tetrachloride (6 ml), triphenylphosphine (108 mg, 0.412 mmol) was added.

The solution was stirred for thirty hours at room temperature.

Evaporation of the organic solvent and purification of the residue by column chromatography (silica gel, elution with cyclohexane ethyl acetate mixtures) gave the title compound as a light yellow oil (168 mg, 77%).

UV (CHCl$_3$) $\lambda_{max}$ 267, 329 nm.

NMR (CDCl$_3$) δ ppm 1.50 (3H, d), 4.00 (1H, dd, J=2.0 and 7.0 Hz), 4.75 (2H, ABq, J=13.5 Hz, separation of inner lines=13 Hz), 5.20 (1H, m), 5.35 (2H, ABq, J=14 Hz, separation of inner lines=8 Hz), 5.26 (2H, s), 5.68 (1H, d, J=2 Hz), 7.52 (2H, d, J=8 Hz), 7.62 (2H, d, J=8 Hz), 8.20 (4H, d, J=8 Hz).

EXAMPLE 20 p-Nitrobenzyl(5R,6S)-6-[1(R)-p-nitrobenzyloxycarbonyloxyethyl]-2-[(1-methyl-1,2,3,4-tetrazol-5-yl)-thiomethyl]-penem-3-carboxylate

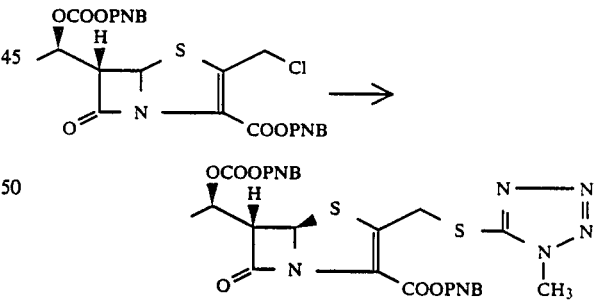

p-Nitrobenzyl(5R,6S)-6-[1(R)-p-nitrobenzyloxycarbonyloxyethyl]-2-chloromethyl-penem-3-carboxylate (150 mg, 0.26 mmol) was dissolved in tetrahydrofuran (5 ml) at 0° C. 1-methyl-5-mercapto-1,2,3,4-tetrazole sodium salt bihydrate (31.3 mg, 0.18 mmol) was added and the resulting solution was stirred for an hour at 0° C. and 2 hours at 25° C. The organic solvent was removed under reduced pressure and the residue chromatographed over silica gel eluting with toluene-ethyl acetate mixtures.

Title compound was obtained as a white foam (152 mg, 89%).

UV (CHCl$_3$) $\lambda_{max}$ 266, 330 nm.

NMR (CDCl$_3$ δ ppm 1.48 (3H, d, J=Hz), 3.84 (1H, dd, J=2.0 and 5.5 Hz), 3.96 (3H, s), 4.69 (2H, ABq, J=14 Hz, separation of inner lines=18 Hz), 5.20 (1H, m), 5.24 (2H, s), 5.27 (2H, ABq, J=13 Hz, separation of inner lines=20 Hz), 5.61 (1H, d, J=2.0 Hz), 7.51 (2H, d, J=8.0 Hz), 7.82 (2H, d, J=8.0 Hz), 8.02 (4H, d, J=8.0 Hz).

EXAMPLE 21 p-Nitrobenzyl(5R,6S)-6-[1(R)-p-nitrobenzyloxycarbonyloxyethyl]-2-(1-methyl-1,2,3,4-tetrazol-5-yl)-thiomethylpenem-3-carboxylate

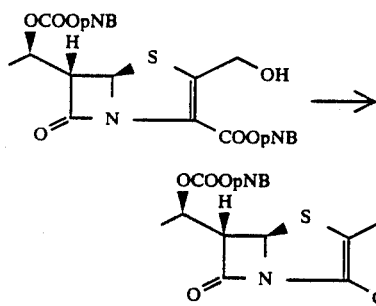

A solution of diethylazodicarboxylate (21.6 μl; 0.137 mmol) and triphenylphosphine (36 mg, 0.137 mmol) in tetrahydrofuran (1.5 ml) was stirred at 0° C. for thirty minutes. To this mixture a solution of p-nitrobenzyl (5R,6S,8R)-6-(1-p-nitrobenzyloxycarbonyloxyethyl)-2-hydroxymethylpenem-3-carboxylate (76.5 mg, 0.137 mmol) and 1-methyl-5-mercapto-1,2,3,4-tetrazole sodium salt (18.9 mg, 0.137 mmol) in tetrahydrofuran (1.0 ml) was added dropwise at 0° C.

The resulting solution was stirred at 0° C. for ten minutes, then concentrated in vacuo and purified by preparative layer chromatography to give the title compound as a white foam (61 mg, 68%).

This material shared the same spectroscopical properties with the sample previously described in Example 20.

EXAMPLE 22 p-Nitrobenzyl(5R6S)-6-[1(R)-p-nitrobenzyloxycarbonyloxymethyl]-2-(1-methyl-1,2,3,4-tetrazol-5-yl)-thiomethyl-penem-3-carboxylate

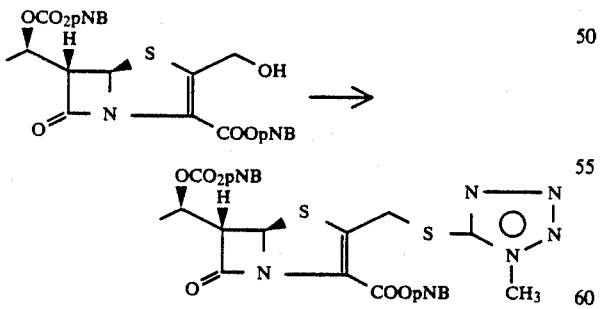

A solution of p-nitrobenzyl(5R,6S)-6-[1(R)-nitrobenzyloxycarbonyloxyethyl]-2-hydroxymethyl-penem-3-carboxylate (300 mg, 0.536 mmol) in acetonitrile (10 ml) was treated with anhydrous 1-methyl-5-mercapto-1,2,3,4-tetrazole and dimethylformamide dineopentyl acetal (1.07 mmol each). After stirring for 3 hours at room temperature, the solvent was removed in vacuo and the residue chromatographed on silica gel to give the title product in low yield.

IR (CH$_2$Cl$_2$) $ν_{max}$ 1795, 1755, 1710.

The product shared the same NMR and UV spectra with the sample obtained as described in Example 20.

EXAMPLE 23

Sodium (5R,6S)-6-[1(R)-hydroxyethyl]-2-[(1-methyl-1,2,3,4-tetrazol-5-yl)-thiomethyl]-penem-3-carboxylate

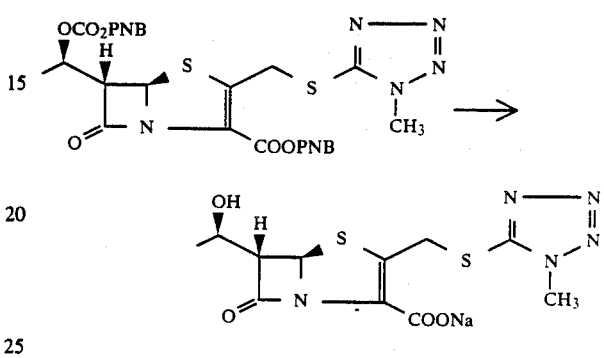

To a solution of p-nitrobenzyl(5R,6S)-6-[1(R)-p-nitrobenzyloxycarbonyloxyethyl]-2-[(1-methyl-1,2,3,4-tetrazol-5-yl)-thiomethyl]-penem-3-carboxylate (100 mg, 0.15 mmol) in THF (1.5 ml) an aqueous 1M solution of NH$_4$Cl (7.5 ml) and iron powder (0.25 g) were added at 0° C. under vigorous stirring.

After 20 minutes a further amount of 1M aqueous ammonium chloride solution (5 ml) and iron powder (1.1 g) were added and stirring was continued for 45 minutes. The mixture was filtered and the filtrate was washed with Et$_2$O (2×30 ml). The organic layer was discarded and the aqueous phase was evaporated in vacuo to dryness. The residue was purified on a reverse phase column eluting with water to obtain (5R,6S)-6-[1(R)-hydroxyethyl]-2-[(1-methyl-1,2,3,4-tetrazol-5-yl)-thiomethyl]-penem-3-carboxylic acid (20 mg), which, by treatment with a molar equivalent amount of sodium hydrogen carbonate and vacuum-drying, was converted into the corresponding sodium salt, identical with the sample obtained in example 13.

EXAMPLE 24 p-Nitrobenzyl(5R,6S)-6-[1(R)-hydroxyethyl]-2-methylsulphonyloxymethyl-penem-3-carboxylate

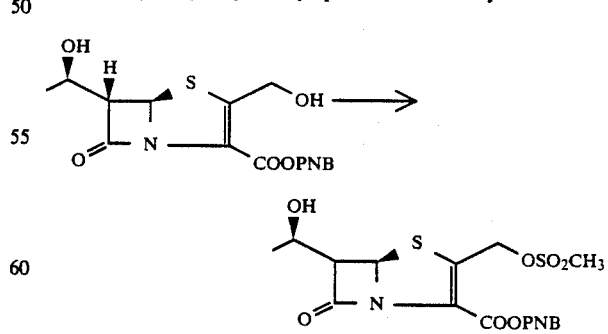

A solution of p-nitrobenzyl(5R,6S)-6-[1(R)-hydroxyethyl]-2-hydroxymethyl-penem-3-carboxylate (100 mg, 0.27 mmol) in a mixture of CH$_2$Cl$_2$ (4 ml) and THF (1 ml) was treated at 0° C. under stirring with Et$_3$N (56 μl, 0.4 mmol) and methanesulphonyl chloride (23 μl, 0.3 mmol) until complete reaction was achieved (TLC monitoring). The solution was diluted with aqueous NaHCO₃ and carefully washed with water.

The aqueous phase was discarded and the dried organic phase was evaporated in vacuo to give the title product as a yellow oil.

NMR (CDCl₃) δ ppm 1.45 (3H, d, J=6.5 Hz), 3.11 (3H, s), 3.84 (1H, dd, J=1.5, 6.1 Hz), 4.25 (1H, m), 5.33 (2H, ABq, J=12 Hz, separation of inner lines=10 Hz), 5.38 (2H, ABq, J=14 Hz, separation of inner lines 24 Hz), 5.75 (1H, d, J=1.5 Hz), 7.61 (2H, d, J=8 Hz), 8.02 (2H, d, J=8 Hz).

EXAMPLE 25 p-Nitrobenzyl(5R,6S)-6-[1(R)-hydroxyethyl]-2-[(1-methyl-1,2,3,4-tetrazol-5-yl)-thiomethyl]-penem-3-carboxylate

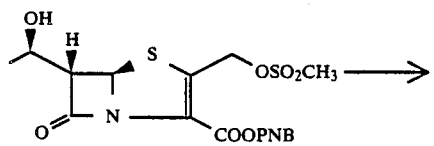

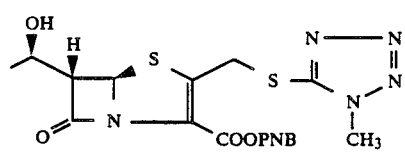

To a solution of p-nitrobenzyl(5R,6S)-6-[1(R)-hydroxyethyl]-2-methylsulphonyloxymethyl-penem-3-carboxylate (70 mg, 0.154 mmol) in ethyl acetate (2 ml), a solution of 1-methyl-5-mercapto-1,2,3,4-tetrazole sodium salt bihydrate (53.6 mg, 0.3 mmol) in THF (5 ml) was added at −70° C. under stirring.

After 1 hour the reaction mixture was let rise to −20° C. and stirred overnight at −20° C.

The solution was then evaporated in vacuo. The resulting solid residue was taken up in ethyl acetate and washed with an aqueous solution of NaHCO₃.

The organic phase was separated, dried over anhydrous Na₂SO₄, filtered and evaporated in vacuo to give a yellow oil which was purified by column chromatography eluting with ethyl acetate cyclohexane mixtures.

The title compound was so obtained as a colourless oil (40 mg, 30% overall yield based upon the 2-hydroxymethyl intermediate).

UV (CHCl₃) λ$_{max}$ 255, 334 nm.

NMR (CDCl₃) δppm 1.38 (3H, d, J=6 Hz), 3.77 (1H, dd, J=1.0 and 6.0 Hz), 3.93 (3H, s), 4.27 (2H, ABq, J=15 Hz, separation of inner lines=16 Hz), 4.77 (2H, ABq, J=15 Hz, separation of inner lines=16 Hz), 5.30 (2H, s), 5.33 (2H, ABq, J=14 Hz, separation of inner lines=9 Hz), 5.64 (1H, d, J=2.0 Hz), 7.56 (2H, d, J=8 Hz), 8.22 (2H, d, J=8 Hz).

EXAMPLE 26

Sodium(5R,6S)-6-[1(R)-hydroxyethyl]-2-(1-methyl-1,2,3,4-tetrazol-5-yl)-thiomethyl-penem-3-carboxylate

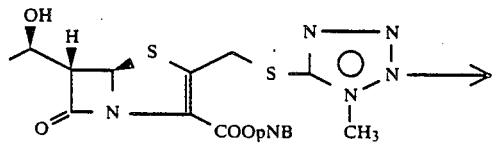

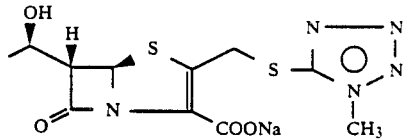

An aqueous 1M solution of NH₄Cl (2 ml) and iron powder (0.1 g) were added to a THF solution of p-nitrobenzyl(5R,6S)-6-[1(R)-hydroxyethyl]-2-(1-methyl-1,2,3,4-tetrazol-5-yl)-thiomethyl-penem-3-carboxylate (40 mg, 0.083 mmol). The mixture was vigorously stirred for 30 minutes at room temperature, after which time a further amount of the reactants, if required (TLC monitoring), was added. When the starting material had disappeared, the mixture was filtered, the filtrate washed with ethyl ether (2×30 ml), concentrated to a small volume under high vacuum and purified on a reverse phase column eluting with water. The title product, identical with the sample described in Example 13, was obtained upon treatment with sodium hydrogen carbonate and freeze-drying, as a white amorphous solid (18 mg, 59%).

EXAMPLE 27

Tert-butyldiphenylsilyl(5R,6S)-6-[1(R)-tert-butyldimethylsilyloxyethyl]-2-hydroxymethyl-penem-3-carboxylate

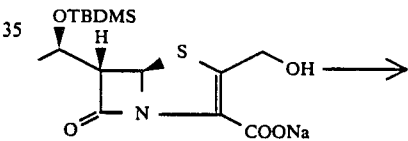

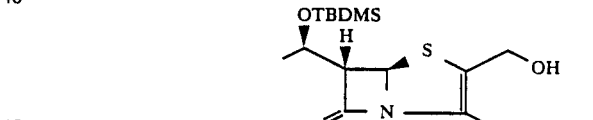

Sodium salt of (5R,6S)-6-[1(R)-tert-butyldimethylsilyloxyethyl]-2-hydroxymethyl-penem-3-carboxylic acid (30 mg, 78.6 mmol) was suspended in anhydrous tetrahydrofuran (4 ml).

Tert-butyldiphenylsilylchloride (20.1 μl, 78.6 mmol) was added at room temperature.

After tirty minutes stirring, triethylamine (5.5 μl, 39.3 mmol) and a further amount of tert-butyldiphenylsilylchloride (10 μl, 39.3 mmol) were added. Within half an hour, the precipitate was completely dissolved. The solution was concentrated and the residue chromatographed over silica gel eluting with cyclohexane-ethyl acetate mixtures to give a colourless oil (30 mg, 64%).

UV (CHCl₃) λ$_{max}$ 331 nm.

IR (CH₂Cl₂) ν$_{max}$ 1790, 1710 cm⁻¹.

NMR (CDCl₃) δppm 0.07 and 0.08 (3H, two s), 0.88 (9H, s), 1.10 (9H, s), 1.24 (3H, d, J=6.0 Hz), 3.50 (1H, t, exch. with D₂O), 3.77 (1H, dd, J=1.5 and 5.0 Hz), 4.24 (1H, m), 4.42 (2H, d, singlet after exch. with D₂O), 5.63 (1H, d, J=1.5 Hz), 7.2–7.8 (10H, m).

EXAMPLE 28

Tert-butyldiphenylsilyl(5R,6S)-6-[1(R)-tert-butyldimethylsilyloxyethyl]-2-(1-methyl-1,2,3,4-tetrazol-5-yl)-thiomethyl-penem-3-carboxylate

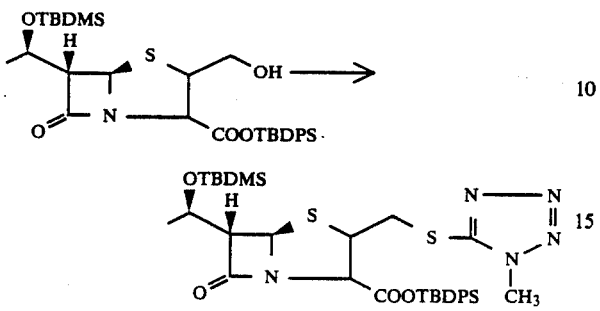

To an ice cooled solution of tert-butyldiphenylsilyl(5R,6S)-6-[1(R)-tert-butyldimethylsilyloxyethyl]-2-hydroxymethyl-penem-3-carboxylate (47 mg, 78.6 mmol) in dry tetrahydrofuran (4.5 ml) triethylamine (11 µl, 78.6 mmol) and methanesulphonyl chloride (6.1 µl, 78.6 mmol) were added. The solution was stirred for ten minutes at 0° C., then 1-methyl-5-mercapto-1,2,3,4-tetrazole sodium salt bihydrate (27.4 mg, 157.2 mmol) was added in a single portion. The resulting mixture was stirred at 0° C. for seventy five minutes.

The residue obtained after evaporation of the solvent was purified by column chromatography (silica gel column, elution with cyclohexane-ethyl acetate mixtures) to give the title compound as a white foam (34 mg, 60%).

UV (CHCl₃) $\lambda_{max}$ 338 nm. This product was directly used for the next step (double desilylation).

EXAMPLE 29

Sodium(5R,6S)-6-[1(R)-hydroxyethyl]-2-(1-methyl-1,2,3,4-tetrazol-5-yl)-thiomethyl-penem-3-carboxylate

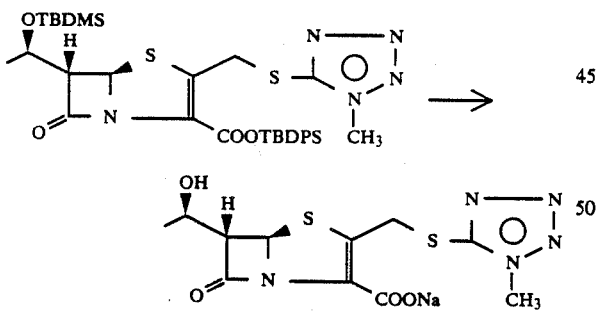

A solution of tert-butyldiphenylsilyl(5R,6S)-6-[1(R)-tert-butyldimethylsilyloxyethyl]-2-(1-methyl-1,2,3,4-tetrazol-5-yl)-thiomethyl-penem-3-carboxylate (34 mg, 0.049 mmol) in tetrahydrofuran (15 ml) was treated with 50% aqueous acetic acid (10 ml). The mixture was stirred for 20 hours at room temperature and then evaporated to dryness in vacuo. The residue was taken up in ice-cold distilled water (1 ml) and sodium hydrogen carbonate was added with stirring to bring the pH to 7.5. The solution was washed with ethyl acetate and then passed through a reverse phase column (LiChroprep. RP-18 Merck) to give the title product as an amorphous solid (4 mg, 22%).

EXAMPLE 30

Acetoxymethyl(5R,6S)-6-[1(R)-tert-butyldimethylsilyloxyethyl]-2-(1-methyl-1,2,3,4-tetrazol-5-yl)-thiomethyl-penem-3-carboxylate

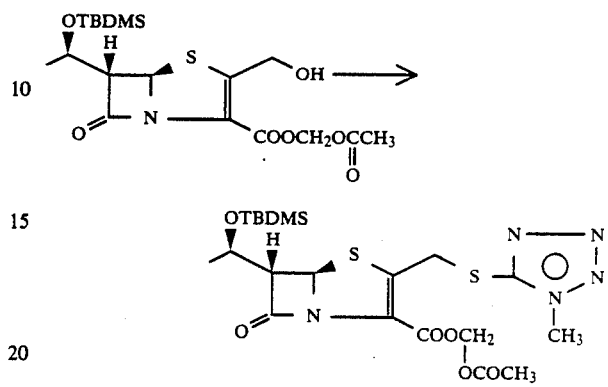

Diethylazodicarboxylate (216 µl, 0.137 mmol) was added to a stirred solution of triphenylphosphine (36 mg, 0.137 mmol) in tetrahydrofuran (0.5 ml) at 0° C. The mixture was stirred at 0° C. for 30 minutes, then added to a solution of acetoxymethyl(5R,6S)-6-[1(R)-tert-butyldimethylsilyloxyethyl]-2-hydroxymethyl-2-penem-3-carboxylate (59 mg, 0.137 mmol) and 1-methyl-5-mercapto-1,2,3,4-tetrazole sodium salt (18.9 mg, 0.137 mmol) in tetrahydrofuran (2 ml) at 0° C. The mixture was stirred at 0° C. for fifteen minutes.

The resulting solution was concentrated under reduced pressure and then purified by column chromatography (silica gel, elution with hexane-ethyl acetate mixture) to give the title compound as a white foam (38 mg, 58%).

UV (CHCl₃) $\lambda_{max}$ 335 nm.

IR (CHCl₃) $\nu_{max}$ 1785, 1760, 1720 cm$^{-1}$.

NMR (CDCl₃) δppm 0.05 (6H, s), 0.87 (9H, s), 1.19 (3H, d, J=6.0 Hz), 2.18 (3H, s), 3.68 (1H, dd, J=2.0 and 4.0 Hz), 3.92 (3H, s), 4.21 (1H, m), 4.72 (2H, ABq, J=14.5 Hz, separation of inner lines=15 Hz), 5.54 (1H, d, J=2.0 Hz), 5.92 (2H, ABq, J=6.0 Hz, separation of inner lines≃1 Hz).

EXAMPLE 31 p-Nitrobenzyl(5R,6S)-6-[1(R)-p-nitrobenzyloxycarbonyloxyethyl]-2-acetoxymethyl-penem-3-carboxylate

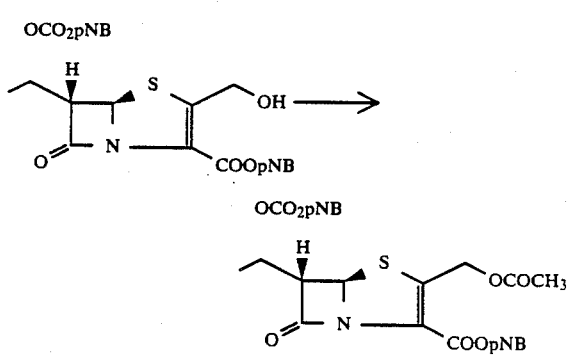

A solution of p-nitrobenzyl(5R,6S)-6-[1(R)-p-nitrobenzyloxycarbonyloxyethyl]-2-hydroxymethyl-penem-3-carboxylate (350 mg, 0.58 mmol) in dry CH₂Cl₂ (5 ml) was sequentially treated with pyridine (140 mg) and acetic anhydride (80 mg) an then stirred at room temperature for six hours. The mixture was washed with aqueous NaHCO$_3$ (3×5 ml) and water (1×5 ml). The dried (Na$_2$SO$_4$) organic phase was evaporated and the oily residue was purified by silica gel chromatography (eluent: cyclohexane-ethyl acetate) to give the title product as a syrup (200 mg).

UV (EtOH 95%) λ$_{max}$ 265 and 321 nm.

IR (CHCl$_3$) ν$_{max}$ 1795, 1750, 1715, 1610 and 1585 cm$^{-1}$.

NMR (CDCl$_3$) δppm 1.50 (3H, d, J=7 Hz), 2.11 (3H, s), 4.01 (1H, dd, J=1.8 and 7.5 Hz), 5.11 and 5.50 (2H, centres of ABq, J=14 Hz), 5.15 (1H, m), 5.24 and 5.38 (2H, centres of ABq, J=12 Hz), 5.28 (2H, s), 5.70 (1H, d, J=1.8 Hz), 7.55 (2H, d, J=8 Hz), 7.64 (2H, d, J=8 Hz), 8.22 (4H, d, two superimposing d, J=8 Hz).

EXAMPLE 32

Sodium(5R,6S)-6-[1(R)-hydroxyethyl]-2-acetoxymethyl-penem-3-carboxylate

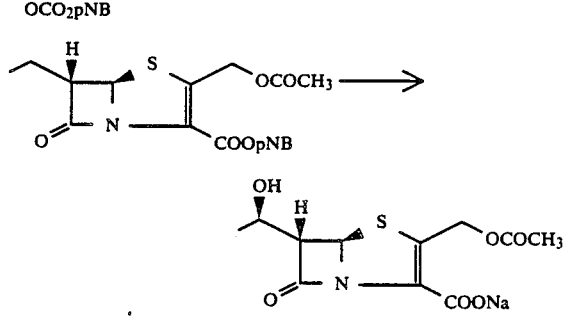

5% Pd/C (0.8 g) was added to a solution of p-nitrobenzyl(5R,6S)-6-[1(R)-p-nitrobenzyloxycarbonyloxyethyl]-2-acetoxymethyl-penem-3-carboxylate (850 mg) in a mixture of ethyl acetate (20 ml) and water (20 ml) containing sodium bicarbonate (100 mg). The mixture was hydrogenated at atmospheric pressure for one hour. A second portion of the catalyst (0.4 g) was then added and the hydrogenation carried on for another 30 minutes. The mixture was filtered, the aqueous phase was washed with ethyl acetate, concentrated at room temperature under vacuum and then passed through a reverse phase column eluting with water. The title compound was thus obtained as an amorphous solid (250 mg).

Elemental analysis Found: C, 40.62; H, 4.14; N, 4.29%. C$_{11}$H$_{12}$NO$_6$SNa.H$_2$O requires C, 40.36; H, 4.31; N, 4.27%.

NMR (D$_2$O) δppm 1.31 (3H, d, J=6.5 Hz), 2.14 (3H, s), 3.94 (1H, dd, J=1.4 and 6.4 Hz), 4.26 (1H, m), 5.28 (2H, ABq, J=14.4 Hz, separation of inner lines=17.6 Hz), 5.68 (1H, d, J=1.4 Hz).

EXAMPLE 33

Sodium (5R,6S)-6-[1(R)-hydroxyethyl]-2-(1-methyl-1,2,3,4-tetrazol-5-yl)-thiomethyl-penem-3-carboxylate

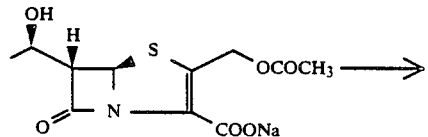

-continued

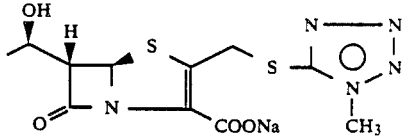

A solution of sodium (5R,6S)-6-[1(R)-hydroxyethyl]-2-acetoxymethyl-penem-3-carboxylate (10 mg, 0.032 mmol) in dry acetonitrile (1 ml) was treated with anhydrous 1-methyl-5-mercapto-1,2,3,4-tetrazole (4.5 mg, 0.04 mmol) followed by acetic acid (1.8 μl, 0.032 mmol). The mixture was refluxed for 90 minutes, then evaporated in vacuo, taken up in distilled water, brought to pH 7.5 with NaHCO$_3$ and fractionated twice on a reverse phase column, eluting with water.

The fractions containing the title product were lyophilized to afford 1.5 mg (12%) of the title product, which displayed the same spectroscopical properties of the sample obtained from Example 13. A fairly large amount of the starting 2-acetoxymethyl-penem was recovered in the fractions following the product.

EXAMPLE 34 p-Nitrobenzyl(5R,6S)-6-[1(R)-p-nitrobenzyloxycarbonyloxyethyl]-2-acetoacetoxymethyl-penem-3-carboxylate

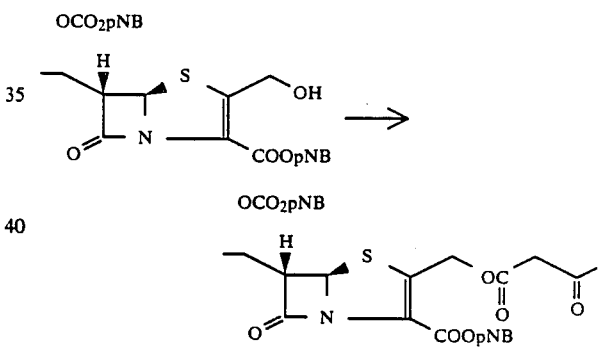

To a solution of p-nitrobenzyl(5R,6S)-6-[1(R)-p-nitrobenzyloxycarbonyloxyethyl]-2-hydroxymethyl-penem-3-carboxylate (420 mg, 0.7 mmol) in dry CH$_2$Cl$_2$ (5 ml), triethylamine (0.05 ml, 0.35 mmol) and diketene (0.02 ml, 1.5 mmol) were sequentially added. After stirring for 1 hour at room temperature, the solution was evaporated in vacuo to leave a brown oil which was taken up with ethyl acetate and washed with water.

The organic layer was separated, dried with anhydrous Na$_2$SO$_4$ and evaporated in vacuo again. The oily residue was chromatographed on silica gel eluting with cyclohexane-ethylacetate mixtures. The title product was so obtained as a colourless oil (260 mg, 55%).

UV (CHCl$_3$) λ$_{max}$ 265, 317 nm.

IR (CHCl$_3$) ν$_{max}$ 1795, 1750, 1720, 1605, 1580 cm$^{-1}$.

NMR (CDCl$_3$) δ ppm 1.52 (3H, d, J=6.5 Hz), 2.31 (3H, s), 3.59 (2H, s), 4.06 (1H, dd, J=2 and 6.5 Hz), 5.04–5.70 (5H, m), 5.51 (2H, s), 5.73 (1H, d, J=2 Hz), 7.55 (2H, d, J=8 Hz), 7.64 (2H, d, J=8 Hz), 8.20 (4H, two superimposing d, J=8 Hz).

EXAMPLE 35

Sodium (5R,6S)-6-[1(R)-hydroxyethyl]-2-acetoacetoxymethyl-penem-3-carboxylate

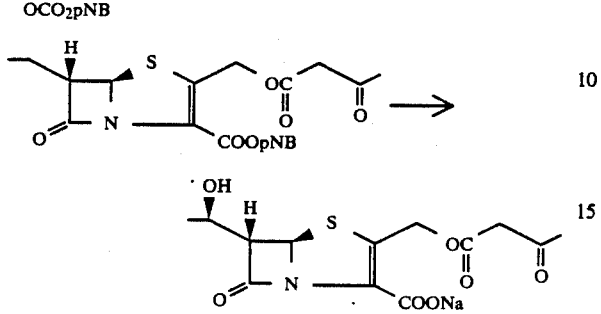

To a solution of p-nitrobenzyl(5R,6S)-6-[1(R)-p-nitrobenzyloxycarbonyloxyethyl]-2-acetoacetoxymethyl-penem-3-carboxylate (250 mg) in ethyl acetate (10 ml), an aqueous solution of sodium bicarbonate (30.9 mg in 10 ml) and 5% Pd/C (200 mg) were added. The resulting mixture was hydrogenated at atmospheric pressure for 1 hour. After this time another portion of the catalyst (100 mg) was added and the reaction carried on until hydrogen was no longer absorbed. The catalyst was filtered, the aqueous phase was separated and washed with ethyl acetate.

The organic phase was discarded and the aqueous phase was evaporated in vacuo. The residue was purified through a reverse phase column eluting with water. The aqueous solution was evaporated leaving the title product as an amorphous solid (40 mg).

UV (EtOH 95%) $\lambda_{max}$ 260 nm ($\epsilon$4630), 305 nm (4890).

NMR (D$_2$O) δ ppm 1.29 (3H, d, J=6.5 Hz), 2.32 (3H, s), 3.92 (1H, dd, J=1.5, 6.0 Hz), 4.24 (1H, m), 5.15–5.53 (2H, centres of ABq, J=15 Hz), 5.65 (1H, d, H=1.5 Hz).

EXAMPLE 36

Sodium (5R,6S)-6-[1(R)-hydroxyethyl]-2-(1-methyl-1,2,3,4-tetrazol-5-yl)-thiomethyl-penem-3-carboxylate

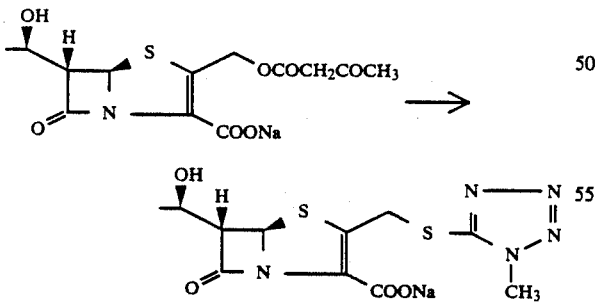

1-Methyl-5-mercapto-1,2,3,4-tetrazole sodium salt dihydrate (45 mg, 0.3 mmol) was added to a buffered (pH 6.8) aqueous solution of sodium (5R,6S)-6-[1(R)-hydroxyethyl]-2-acetoacetoxymethyl-penem-3-carboxylate (35 mg, 0.1 mmol). The solution was heated under nitrogen for 30 minutes at 52° C., to give a crude mixture of the unreacted starting materials and of the title product, which was fractionated on a reverse phase column (LiChroprep. RP-18 Merck) eluting with water.

EXAMPLE 37 p-Nitrobenzyl(5R,6S)-6-[1(R)-p-nitrobenzyloxycarbonyloxyethyl]-2-[1(2-aminocarbonylethyl)-1,2,3-4-tetrazol-5-yl]-thiomethyl-penem-3-carboxylate

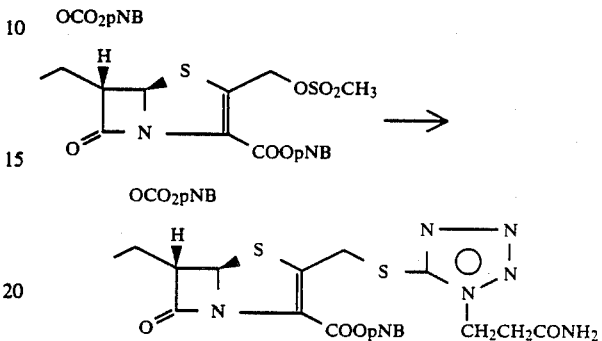

To a solution of p-nitrobenzyl(5R,6S)-6-[1(R)-p-nitrobenzyloxycarbonyloxyethyl]-2-mesyloxymethyl-2-penem-3-carboxylate (38 mg, 0.06 mmol) in dry THF (5 ml), 1-(2-aminocarbonylethyl)-5-mercaptotetrazole triethylammonium salt (80 mg, 0.3 mmol) was added at room temperature. After half an hour the reaction mixture was evaporated in vacuo. The residue was chromatographed on silica gel eluting with cyclohexane-ethyl acetate mixture yielding the title product as a syrup.

UV (CHCl$_3$) $\lambda_{max}$ 266 and 332 nm.

IR (CHCl$_3$) $\lambda_{max}$ 3500, 3400, 1795, 1750, 1710–1695, 1605 cm$^{-1}$.

NMR (CDCl$_3$) δ ppm 1.47 (3H, d, J=7 Hz), 2.7 (2H, t, J=7 Hz), 3.83 (1H, dd, J=2 and 5.5 Hz), 4.3–5.0 (4H, m), 5.2 (1H, m), 5.25 (2H, s), 5.3 (2H, center of Abq), 5.62 (1H, d, J=2 Hz), 7.5 and 7.81 (each 2H, d, J=8 Hz), 8.0 (4H, two superimposing d, J=8 Hz).

MS (FD) m/e 714 (M+). C$_{28}$H$_{26}$N$_8$O$_{11}$S$_2$ requires M, 714.

EXAMPLE 38

Sodium (5R,6S)-6-[1(R)-hydroxyethyl]-2-[1-(2-aminocarbonylethyl)-1,2,3,4-tetrazol-5-yl]-thiomethyl-penem-3-carboxylate

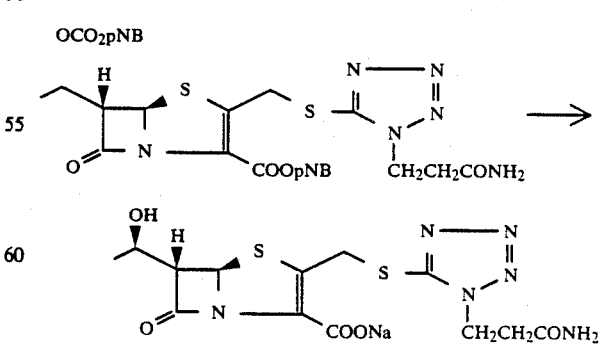

A solution of p-nitrobenzyl(5R,6S)-6-[1(R)-p-nitrobenzyloxycarbonyloxyethyl]-2-[1-(2-aminocarbonylethyl)-1,2,3,4-tetrazol-5-yl]-thiomethyl-penem-3-carboxylate (100 mg, 0.14 mmol) in acetonitrile (5 ml)

was treated with a solution of Na$_2$S$_2$O$_4$ (73 mg, 0.42 mmol) and NaHCO$_3$ in distilled water (4.2 ml).

The mixture was stirred at room temperature with TLC monitoring. When the reaction was almost completed the solvent was evaporated in vacuo, the aqueous solution washed with ethyl acetate and then passed through a reverse phase column to afford the title product.

UV (H$_2$O) λ315 nm.

IR (KBr) ν3400, 1770 and 1695 and 1610 cm$^{-1}$.

MS (FD) m/e (free acid) 400 (M+). C$_{13}$H$_{16}$N$_6$O$_5$S$_2$ requires M, 400.

By proceeding analogously, sodium (5R,6S)-6-[1(R)-hydroxyethyl]-2-[1-(2-aminocarbonylmethyl)-1,2,3,4-tetrazol-5-yl]-thiomethyl-penem-3-carboxylate was obtained.

EXAMPLE 39

Sodium (5R,6S)-6-[1(R)-hydroxyethyl]-2-(5-methyl-1,3,4-thiadiazol-2-yl)-thiomethyl-penem-3-carboxylate

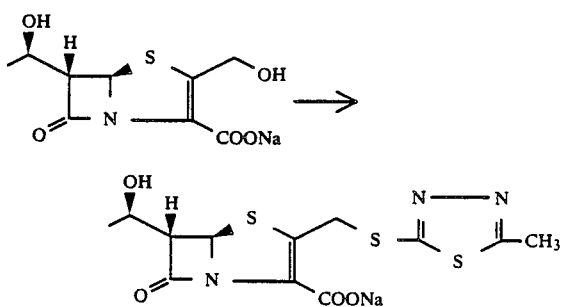

Tert-butyldiphenylsilyl chloride (0.1 ml) was added to a suspension of sodium (5R,6S)-6-[1(R)-hydroxyethyl]-2-hydroxymethyl-penem-3-carboxylate (100 g) in anhydrous tetrahydrofuran. After stirring for 2 hours at room temperature the undissolved matter was filtered off and the filtrate, cooled at −30° C., was treated with methanesulphonyl chloride (0.03 ml) followed, after 30', by a solution of 5-methyl-2-mercapto-1,3,4-thiadiazole sodium satl (60 mg) in tetrahydrofuran.

The mixture was kept overnight at −30° C., then evaporated in vacuo, partitioned between EtOAc and water, and the organic phase evaporated again to give the crude tert-butyldiphenylsilyl ester of the title product. Desilylation with aqueous acetic acid and purification as described in Example 14 gave the final compound as an amorphous solid.

UV (H$_2$O) ν$_{max}$ 314 nm.

NMR (D$_2$O) δ ppm 1.37 (3H, d), 2.77 (3H, s), 3.87 (1H, dd), (4.30 (1H, m), 4.62 (2H, ABq), 5.62 (1H, d).

EXAMPLE 40 p-Nitrobenzyl(5R,6S)-6-[1(R)-hydroxyethyl]-2-[1-(2-cyanoethyl)-1,2,3,4-tetrazol-5-yl]-thiomethyl-penem-3-carboxylate

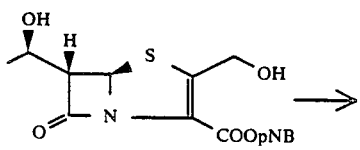

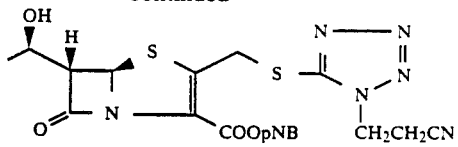

p-Nitrobenzyl(5R,6S)-6-[1(R)-hydroxyethyl]-2-hydroxymethyl-penem-3-carboxylate (37 mg, 0.1 mmol) was added to a stirred solution of N,N-diisopropylethylamine (35 μl, 0.2 mmol) in dry dichloromethane (1 ml). Trifluoromethane sulphonic anhydride (25 μl, 0.15 mmol) was then added, the mixture was stirred 20 min at room temperature, cooled in an ice-bath and treated with a further amount of diisopropylethylamine (26 μl, 0.15 mmol), immediately followed by 5-mercapto-1-(2-cyanoethyl)-1,2,3,4-tetrazole (23 mg, 0.15 mmol). After 2 hours at 0° C. ethyl acetate (10 ml) was added, and the resulting solution was sequentially washed with water, 5% aqueous solution of citric acid and 5% aqueous solution of sodium hydrogen carbonate. The organic layer was dried over Na$_2$SO$_4$, concentrated in vacuo and the residue was fractionated by silica gel chromatography (ethyl acetate-cyclohexane mixture) to yield the title compound (35 mg, 68%) as a foam.

IR (CHCl$_3$) ν$_{max}$ 2240, 1795, 1755, 1710 cm$^{-1}$.

NMR (CDCl$_3$) δ ppm 1.37 (3H, d, J=7 Hz), 3.20 (2H, t, J=7 Hz), 3.77 (1H, dd, J=2 and 6 Hz), 4.30 (1H, m), 4.62 (2H, t, J=7 Hz), 4.8 (2H, ABq, J=15 Hz), 5.30 (4H, s+ABq), 5.65 (1H, d, J=2 Hz), 7.6 and 8.23 (each 2H, d, J=8 Hz).

EXAMPLE 41

Sodium(5R,6S)-6-[1(R)-hydroxyethyl]-2-[1-(2-cyanoethyl)-1,2,3,4-tetrazol-5-yl]-thiomethyl-penem-3-carboxylate

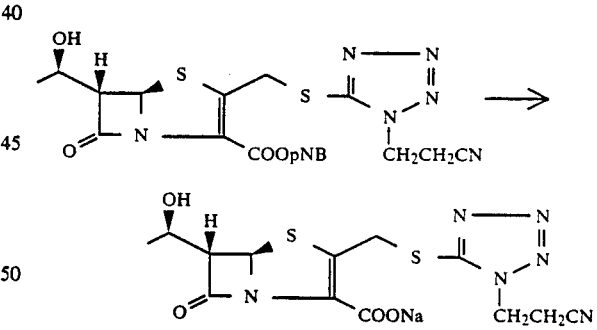

p-Nitrobenzyl(5R,6S)-6-[1(R)-hydroxyethyl]-2-[1-(2-cyanoethyl)-1,2,3,4-tetrazol-5-yl]-thiomethyl-penem-3-carboxylate (35 mg, 0.068 mmol) dissolved in tetrahydrofuran (15 ml) was treated with 1M aqueous NH$_4$Cl (1.5 ml) and iron powder (0.1 g) under vigorous stirring. After 30 min., the filtrate was evaporated in vacuo and passed through a reverse phase column eluting with water, thus obtaining 12 mg (45%) of the free acid corresponding to the title product:

MS (FD) m/e 382 (M+). C$_{13}$H$_{14}$N$_6$O$_4$S$_2$ requires M, 382.

Treatment of the free acid with a molar equivalent amount of sodium hydrogen carbonate and freeze-drying afforded the corresponding sodium salt [UV (H$_2$O) λmax 315 nm].

By proceeding analogously, sodium(5R,6S)-6-[1(R)-hydroxyethyl]-2-[1-(2-cyanomethyl)-1,2,3,4-tetrazol-5-yl]-thiomethyl-penem-3-carboxylate was obtained.

EXAMPLE 42

(5R,6S)-6-[1(R)-hydroxyethyl]-2-(5-carboxymethylthio-1,3,4-thiadiazol-2-yl)-thiomethyl-penem-3-carboxylic acid, disodium salt

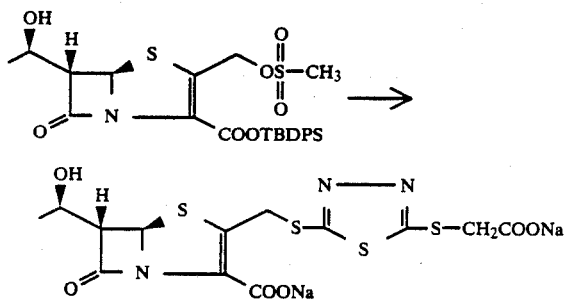

A solution of 2-mercapto-5-carboxymethylthio-1,3,4-thiadiazole (41.6 mg, 0.2 mmol) and triethylamine (56 μl, 0.4 mmol) in anhydrous tetrahydrofuran was added at −30° C. under argon to a solution of tert-butyldiphenylsilyl(5R,6S)-6-[1(R)-hydroxyethyl]-2-methanesulphonyloxymethyl-penem-3-carboxylate (85 g, 0.15 mmol) in the same solvent. After stirring for 5 hours at −30° C., the reaction mixture was concentrated in vacuo, taken up in ethyl acetate and extracted with water.

The organic layer was discarded, the aqueous layer was made acidic with acetic acid and extracted twice with fresh ethyl acetate. This extract was dried ($Na_2SO_4$), concentrated, taken up in THF (3 ml) and stirred for 2 hours with 35% aqueous acetic acid. The reaction mixture was concentrated under high vacuum, treated with a saturated solution of $NaHCO_3$ to a pH of 7.5 and fractionated by a reverse phase column, eluting with water, thus obtaining the title compound (22 mg, 32%).

UV ($H_2O$) $\lambda_{max}$ 314 nm

NMR ($D_2O$) δ ppm 1.25 (3H, d), 3.85 (1H, dd, J=1.5 and 6 Hz), 3.97 (2H, s), 4.2 (1H, m), 4.55 (2H, s), 5.57 (1H, d, J=1.5 Hz).

By proceeding analogously, (5R,6S)-6-[1(R)-hydroxyethyl]-2-(5-carboxymethyl-1,3,4-thiadiazol-2-yl)-thiomethyl-penem-3-carboxylic acid, disodium salt was obtained.

EXAMPLE 43

Sodium(5R,6S)-6-[1(R)-hydroxyethyl]-2-(1H-1,2,3-triazol-5-yl)-thiomethyl-penem-3-carboxylate

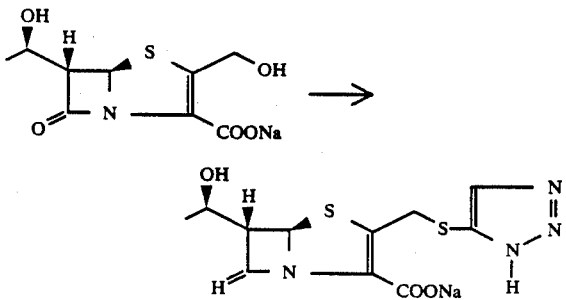

Sodium(5R,6S)-6-[1(R)-hydroxyethyl]-2-hydroxymethyl-penem-3-carboxylate (80 mg, 0.3 mmol) was sequentially treated with tert-butyldiphenylsilylchloride (78 μl), triethylamine (42 μl), methanesulphonylchloride (24 μl) and finally with 1H-5-mercapto-1,2,3-triazole sodium salt (43 mg, 0.35 mmol) by following the experimental procedure described in Example 14.

The so-obtained silyl ester of the title product was directly cleaved with acetic acid-water to afford, after treatment with aqueous $NaHCO_3$ and purification through a LiChroprep RP-18 column, the desired sodium salt (49 mg, 47%).

UV ($H_2O$) $\lambda_{max}$ 314 nm.

IR (KBr) $\nu_{max}$ 3420, 1770, 1610 cm$^{-1}$.

MS (FD) m/e (free acid) 328 (M$^+$). $C_{11}H_{12}N_4O_4S_2$ requires M, 328.

EXAMPLE 44

Acetoxymethyl(5R,6S)-6-[1(R)-hydroxyethyl]-2-[1-(2-dimethylaminoethyl)-1,2,3,4-tetrazol-5-yl]-thiomethyl-penem-3-carboxylate

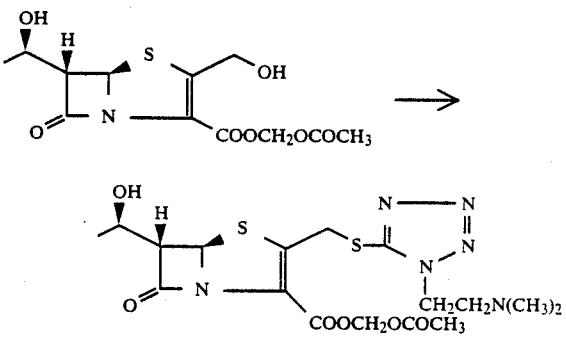

Triethylamine (42 μg, 0.3 mmol) and methanesulphonylchloride (17 μl, 0.22 mmol) were sequentially added to a cold (0° C.) solution of acetoxymethyl (5R,6S)-6-[1(R)-hydroxyethyl]-2-hydroxymethyl-penem-3-carboxylate (60 mg, 0.2 mmol) in a mixture of dichloromethane (4 ml) and tetrahydrofuran (1 ml). When the starting material had disappeared (TLC), the solution was washed with aqueous $NaHCO_3$, then with water, dried and evaporated. The residue was dissolved in ethyl acetate (5 ml), cooled at −30° C. and treated with a solution of 5-mercapto-1-(2-dimethylaminoethyl)-1,2,3,4-tetrazole hydrochloride (63 mg, 0.3 mmol) and triethylamine (84 μl, 0.6 mmol) in tetrahydrofuran (1 ml). The mixture was stirred overnight at −20° C., warmed up to room temperature, washed with water, dried ($Na_2SO_4$) and evaporated to give a residue which was purified by reverse phase chromatography (acetonitrile-water mixture as eluant). The title product was thus obtained as a crisp foam (58 mg, 61%).

UV (EtOH) $\lambda_{max}$ 335 nm.

IR (nujol) $\nu_{max}$ 1785, 1760, 1720 cm$^{-1}$.

NMR (EtOH-d$_6$) δ ppm 1.45 (3H, d, J=6.5 Hz), 2.9 (6H, s), 3.65 (3H, t+dd), 4.10 (1H, m), 4.7 (5H, t+Abq), 5.55 (1H, d, J=1.5 Hz), 5.9 (2H, ABq, J=6.0 Hz).

EXAMPLE 45

(5R,6S)-6-[1(R)-hydroxyethyl]-2-(1-carboxymethyl-1,2,3,4-tetrazol-5-yl)-thiomethyl-penem-3-carboxylic acid disodium salt

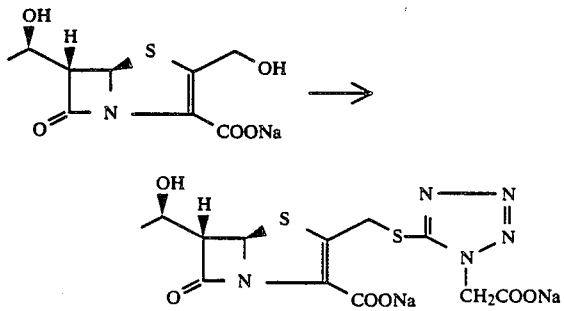

By following the experimental procedure described in Example 14, sodium(5R,6S)-6-[1(R)-hydroxyethyl]-2-hydroxymethyl-penem-3-carboxylate (100 mg, 0.37 mmol) was sequentially esterified with tert-butyldiphenylsilylchloride, mesylated, allowed to react with 1-carboxymethyl-1,2,3,4-tetrazole-5-thiol (64 mg, 0.4 mmol) in the presence of diisopropylethylamine (0.14 ml, 0.8 mmol), and the silyl ester was eventually hydrolysed by a mixture of THF—$H_2O$—AcOH. Work-up and purification through a reverse phase column afforded the title compound (40 mg, 25%).

UV ($H_2O$) $\lambda_{max}$ 315 nm.

NMR ($D_2O$) δ ppm 1.28 (3H, d, 6.3 Hz), 3.85 (1H, dd, J=1.4 and 6.3 HZ), 4.2 (1H, m), 4.4 (2H, ABq), 5.3 (2H, s), 5.60 (1H, d, J=1.4 Hz).

EXAMPLE 46

(5R,6S)-6-[1(R)-hydroxyethyl]-2-[1(2-carboxyethyl)-1,2,3,4-tetrazol-5-yl]-thiomethyl-penem-3-carboxylic acid, disodium salt

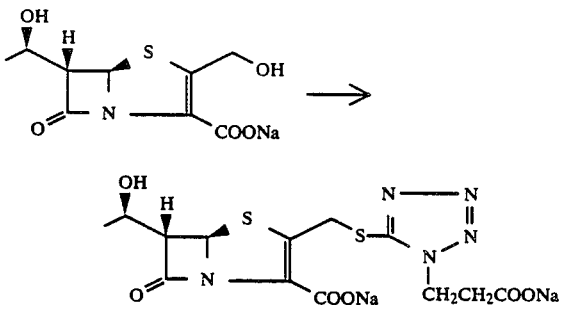

When 5-mercapto-1-(2-carboxyethyl)-1,2,3,4-tetrazole was used in place of 5-mercapto-1-carboxymethyl-1,2,3,4-tetrazole, the procedure described in the preceeding example gave the title compound.

UV ($H_2O$) $\lambda_{max}$ 315 nm.

NMR ($D_2O$) δ ppm 1.3 (3H, d), 2.85 (2H, t), 3.9 (1H, dd), 4.2 (1H, m), 4.4 (4H, m), 5.58 (1H, d, J=1.4 Hz).

MS (FD) m/e (free acid) 401 ($M^+$). $C_{13}H_{15}N_5O_6S_2$ requires M, 401.

EXAMPLE 47 p-Nitrobenzyl(5R,6S)-6-[1(R)-p-nitrobenzyloxycarbonyloxyethyl]-2-(1-pyridinium)-methyl-penem-3-carboxylate, chloride

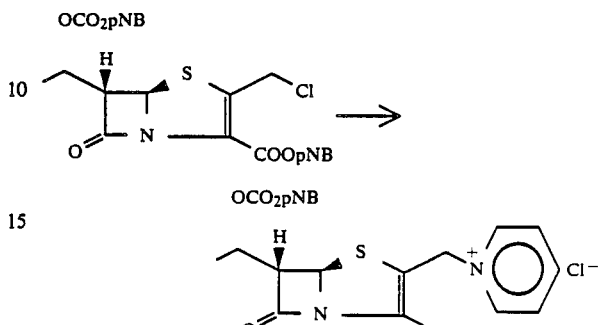

A solution of p-nitrobenzyl(5R,6S)-6-[1(R)-p-nitrobenzyloxycarbonyloxyethyl]-2-chloromethyl-penem-3-carboxylate (58 mg, 0.1 mmol) in dry DMF (0.2 ml) was treated with potassium iodide (0.8 mg) and pyridine (0.1 ml). The mixture was stirred for 40 hours at room temperature. Ethyl ether was added with stirring to precipitate a brownish powder which was collected, washed with ether and purified through a reverse phase column (acetonitrile-water as eluants) to give the title product.

UV (EtOH) $\lambda_{max}$ 264, 330 $cm^{-1}$.

IR (KBr) $\nu_{max}$ 1795, 1750, 1710 $cm^{-1}$.

EXAMPLE 48

(5R,6S)-6-[1(R)-hydroxyethyl]-2-(4-carbamoyl-1-pyridinium)-methyl-penem-3-carboxylate

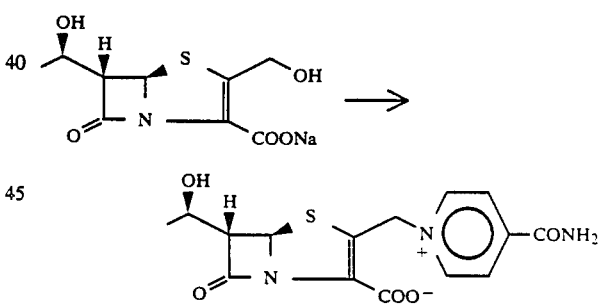

A suspension of sodium(5R,6S)-6-[1(R)-hydroxyethyl]-2-hydroxymethyl-penem-3-carboxylate (100 mg, 0.37 mmol) in dry tetrahydrofuran was stirred with tert-butyldiphenylsilyl chloride (96 μg, 0.37 mmol) for 2 hours at room temperature. The undissolved matter was filtered off and the filtrate was treated at −20° C. with trifluoromethanesulphonic anhydride (67 μl, 0.4 mmol) and triethylamine (55 μl, 0.4 mmol). After 30 min, a solution of nicotinamide (49 mg, 0.4 mmol) in anhydrous DMF was dropped in, and the resulting mixture was stirred overnight at room temperature. Ethy acetate (10 ml) and saturated aqueous NaCl solution (5 ml) were then added. The organic layer was separated, washed again with brine, dried ($Na_2SO_4$) and then stirred for 2 hours in dry THF containing 18-Crown-6 (5 mg) and anhydrous KF (10 mg). The mixture was evaporated to a small volume and the residue triturated with ethyl ether. The solid was collected, dissolved in distilled water and purified on a reverse phase column, eluting with water to give the title product.

NMR (D$_2$O) δ ppm 1.30 (3H, d, J=6.5 Hz), 3.90 (1H, dd, J=1.4 and 6.5 Hz), 4.22 (1H, m), 5.36–5.66 (2H, ABq), 5.60 (1H, d, J=1.4 Hz), 8.30–9.08 (4H, m).

EXAMPLE 49

(5R,6S)-6-[1(R)-hydroxyethyl]-2-(1-sulphomethyl-1,2,3,4-tetrazol-5-yl)-thiomethyl-penem-3-carboxylic acid, disodium salt

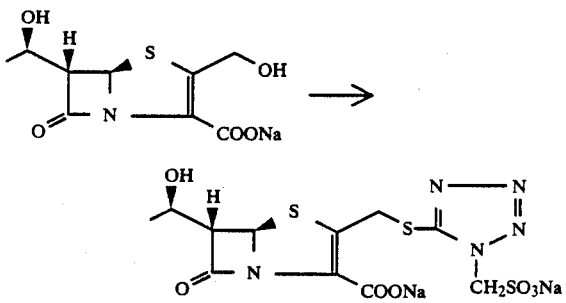

Sodium(5R,6S)-6-[1(R)-hydroxyethyl]-2-hydroxymethyl-penem-carboxylate (80 mg, 0.3 mmol) in dry THF was stirred with tert-butyldiphenylsilyl chloride (78 μl) for 2 hours. The insoluble matters were filtered off, the filtrate was cooled to −30° C., treated with NEt$_3$ (42 μl) and methanesulphonyl chloride (25 μl) and stirred for a further 10 min at −20° C., after which time 1-sulphomethyl-1,2,3,4-tetrazole-5-thiol disodium salt (72 mg, 0.3 mmol) was added portionwise. The mixture was stirred for 6 hours at −20° C., then evaporated in vacuo and triturated with ether. The collected solid was taken up in a mixture of THF, water and acetic acid (2:2:1), stirred for 2 hours at room temperature, evaporated in vacuo, taken up with 2% aqueous NaHCO$_3$ solution, washed with ethyl acetate and then passed through a reverse phase column, to give the title product.

UV (H$_2$O) λ$_{max}$ 315 nm.

IR (KBr) ν$_{max}$ 3400, 1770 and 1610 cm$^{-1}$.

By proceeding analogously, (5R,6S)-6-[1(R)-hydroxyethyl]-2-(1-sulphoethyl-1,2,3,4-tetrazol-5-yl)-thiomethyl-penem-3-carboxylic acid disodium salt was prepared.

By omitting the final treatment with aqueous NaHCO$_3$ the corresponding free acids were obtained: (5R,6S)-6-[1(R)-hydroxyethyl]-2-(1-sulphomethyl-1,2,3,4-tetrazol-5-yl)-thiomethyl-penem-3-carboxylic acid.

[MS (FD) m/e 423 (M+). C$_{11}$H$_{13}$N$_5$O$_7$S$_3$ requires M, 423]; and (5R,6S)-6-[1(R)-hydroxyethyl]-2-(1-sulphoethyl-1,2,3,4-tetrazol-5-yl)-thiomethyl-penem-3-carboxylic acid.

EXAMPLE 50

(5R,6S)-6-[1(R)-hydroxyethyl]-2-[1-(2-sulfoaminoethyl)-1,2,3,4-tetrazol-5-yl]-thiomethyl-penem-3-carboxylic acid, disodium salt

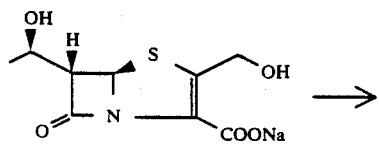

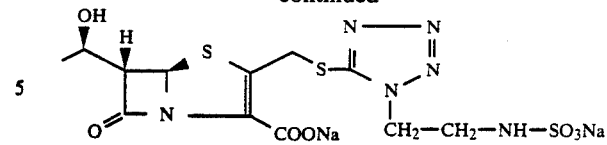

By following the same procedure described in Example 49, but using 5-mercapto-1-(2-sulfoaminoethyl)-1,2,3-4-tetrazole disodium salt instead of 5-mercapto-1-sulphomethyl-1,2,3,4-tetrazole, sodium(5R,6S)-6-[1(R)-hydroxyethyl]-2-hydroxymethyl-penem-3-carboxylate was converted into the title product in 20% isolated yield.

UV (H$_2$O) λ$_{max}$ 314 nm.

IR (KBr) ν$_{max}$ 3420, 1770 and 1610 cm$^{-1}$.

MS (FD) m/e (free acid) 452 (M+). C$_{12}$H$_{13}$N$_6$O$_7$S$_3$ requires M, 452.

EXAMPLE 51

(5R,6S)-6-[1(R)-hydroxyethyl]-2-(4-carboxymethyl-5-methyl-1,3-thiazol-2-yl)-thiomethyl-penem-3-carboxylic acid, disodium salt

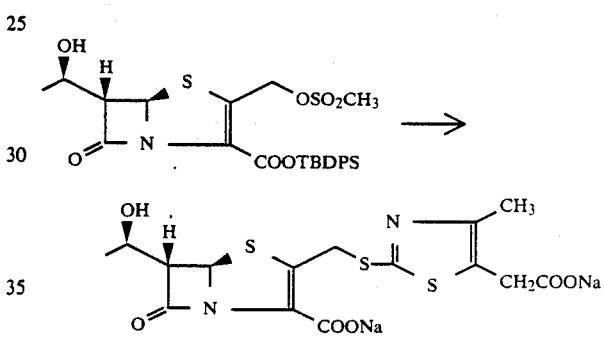

2-mercapto-4-carboxymethyl-5-methyl-1,3-thiazole disodium salt (58 mg, 0.25 mmol) was added portionwise at −30° C. to a stirred solution of tert-butyldiphenylsilyl(5R-6S)-6-[1(R)-hydroxyethyl]-2-methanesulphonyloxymethyl-penem-3-carboxylate (110 mg, 0.2 mmol) in dry tetrahydrofuran. After 6 hours at −30° C. and 3 hours at room temperature the mixture was partitioned between EtOAc and aqueous NaHCO$_3$. The aqueous layer was made acidic with ice-cold, 5% citric acid and immediately extracted with fresh ethyl acetate. Hydrolysis of the tert-butyldiphenylsilyl ester was accomplished with 50% aqueous acetic acid (TLC monitoring). The excess HOAc was removed in vacuo and the residue was completely neutralized with aqueous NaHCO$_3$.

Elution with water from a reverse phase column and freeze-drying afforded the title product.

Elemental analysis Found: C, 36.43; H, 3.67; N, 5.52% C$_{15}$H$_{14}$N$_2$O$_6$S$_3$Na$_2$.2H$_2$O requires C, 36.28; H, 3.65; N, 5.64%.

EXAMPLE 52

Sodium(5R,6S)-6-[1(R)-hydroxyethyl]-2-(tetrazolo[1,5-b]pyridazin-6-yl)-thiomethyl-penem-3-carboxylate

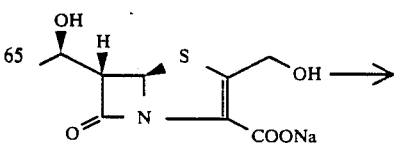

-continued

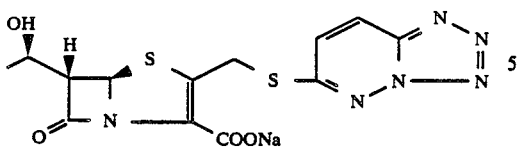

By following the experimental procedure described in Example 14, sodium(5R,6S)-6-[1(R)-hydroxyethyl]-2-hydroxymethyl-penem-3-carboxylate (80 mg, 0.3 mmol) was allowed to react with tert-butyldiphenylsilylchloride (78 μl), methanesulphonylchloride (24 μl), triethylamine (42 μl) and 6-mercaptotetrazolo-[1,5-b]-pyridazine sodium salt (57 mg, 0.35 mmol). Desilylation was finally achieved by stirring a solution of the crude product in THF (2 ml) with 50% aqueous acetic acid (1.5 ml) for 90 min at room temperature. The reaction mixture was concentrated in vacuo, taken up in aqueous NaHCO₃ and passed through a reverse phase column, eluting with water, to afford the title product.

IR (KBr) $v_{max}$ 3430, 1765, 1605 cm$^{-1}$.

NMR (D₂O) δ ppm 1.24 (3H, d), 3.82 (1H, dd, J=1.5 and 6.1 Hz), 4.22 (1H, m), 4.66 and 4.96 (each 1H, d, J=12 Hz), 5.60 (1H, d, J=1.5 Hz), 7.68 (1H, d, J=9.6 Hz), 8.38 (1H, d, J=9.6 Hz).

EXAMPLE 53

(5R,6S)-6-[1(R)-hydroxyethyl]-2-(8-carboxytetrazolo-[1,5-b]-pyridazin-6-yl)-thiomethyl-penem-3-carboxylic acid, disodium salt

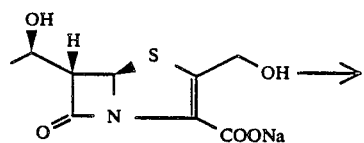

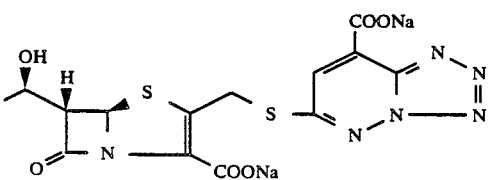

The title compound was obtained as an amorphous powder (27% yield) when 6-mercapto-8-carboxytetrazolo-[1,5-b]-pyridazine (74 mg, 0.4 mmol) and triethylamine (112 μl, 0.8 mmol) were used in the preceeding example instead of 6-mercaptotetrazolo-[1,5-b]-pyridazine sodium salt.

NMR (D₂O) δ ppm 1.3 (3H, d), 3.9 (1H, dd), 4.2 (1H, m), 4.45 (2H, ABq), 5.6 (1H, d), 8.2 (1H, s).

EXAMPLE 54

Sodium(5R,6S)-6-[1(R)-hydroxyethyl]-2-(8-aminotetrazolo-[1,5-b]-pyridazin-6-yl)-thiomethyl-penem-3-carboxylate

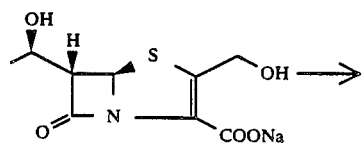

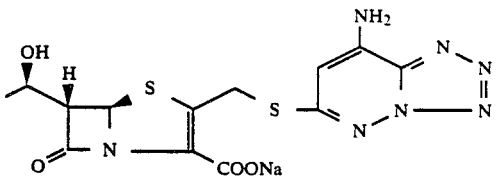

Sodium(5R,6S)-6-[1(R)-hydroxyethyl]-2-hydroxymethyl-penem-3-carboxylate (80 mg, 0.3 mmol) was converted into its tert-butyldiphenylsilyl ester by stirring for 2 hours with tert-butyldiphenylsilylchloride (78 μl, 0.3 mmol) in anhydrous THF. Diphenyl chlorophosphate (62 μl, 0.3 mmol) and triethylamine (42 μl, 0.3 mmol) were added at −20° C. to the crude mixture, and the whole was stirred for 15 min in the cold and 30 min at room temperature. The solution was cooled again to −20° C. and treated with a solution of 8-amino-6-mercaptotetrazolo-[1,5-b]-pyridazine (50.5 mg, 0.3 mmol) and triethylamine (83 μl, 0.6 mmol) in THF (3 ml). After overnight stirring at −20° C., the reaction mixture was concentrated in vacuo and partitioned between EtOAc and aqueous NaHCO₃. The organic layer, containing the tert-butyldiphenylsilyl ester of the title product, was dried over Na₂SO₄, freed from the solvent and the residue was directly taken up in a mixture of THF, AcOH and H₂O (1:1:1, 5 ml). After completion of the silyl ester hydrolysis (TLC monitoring), the crude mixture was concentrated in vacuo, made neutral with enough aqueous NaHCO₃ and then purified by reverse phase column chromatography, thus obtaining the title product as a foam.

IR (KBr) $v_{max}$ 1760, 1660, 1625 cm$^{-1}$.

NMR (D₂O) δ ppm 1.30 (3H, d), 3.77 (1H, dd, J=1.8 and 6.5 Hz), 4.18 (1H, m), 4.55 (2H, br s), 5.50 (1H, d, J=1.8 Hz), 6.50 (1H, s).

EXAMPLE 55

(5R,6S)-6-[1(R)-hydroxyethyl]-2-(2-methyl-5-oxo-6-hydroxy-2,5-dihydro-1,2,4-triazin-3-yl)-thiomethyl-penem-3-carboxylic acid, disodium salt

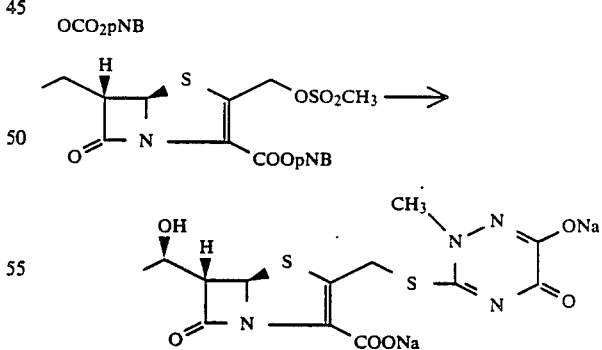

A solution of p-nitrobenzyl(5R,6S)-6-[1(R)-p-nitrobenzyloxycarbonyloxyethyl]-2-methanesulphonyloxymethyl-penem-3-carboxylate (63 mg, 0.1 mmol) in dry THF (3 ml), cooled to −30° C., was treated with a solution of 2-methyl-3-mercapto-5-oxo-6-hydroxy-2,5-dihydro-1,2,4-triazine (24 mg, 0.15 mmol) and triethylamine (42 μl, 0.3 mmol) in the same solvent.

After 30 min at −30° C., the mixture was allowed to reach room temperature, and then concentrated in vacuo. The residue was taken up with ethyl acetate, washed with water, dried (Na₂SO₄) and evaporated.

After purification by reverse phase chromatograpgy, the so-obtained di-p-nitrobenzyl intermediate, dissolved in THF (1 ml) was vigorously stirred with 1M aqueous solution of NH₄Cl (5 ml) and iron powder (0.3 g).

Upon completion of the reaction (TLC monitoring), the mixture was treated with aqueous NaHCO₃, filtered, the filtrate washed with ethyl acetate, concentrated to a syrup which was purified through a LiChroprep. RP-18 column (water as eluant), thus affording the title product.

NMR (D₂O) δ ppm, (200 MHz apparatus) 1.25 (3H, d), 3.65 (3H, s), 3.82 (1H, dd, J=1.6 and 5.9 Hz), 4.20 (1H, m), 4.59 (2H, ABq, J=14.5 Hz, separation of inner lines 14.9 Hz), 5.55 (1H, d, J=1.6 Hz).

By omitting the treatment with NaHCO₃, and purifying directly the hydrolysis mixture, the corresponding (5R,6S)-6-[(1(R)-hydroxyethyl]-2-(2-methyl-5-oxo-6-hydroxy-2,5-dihydro-1,2,4-triazin-3-yl)-thiomethyl-penem-3-carboxylic acid was obtained.

Similarly, the free acid of the compounds described in the examples 13, 38, 41, 42, 44, 45, 46, 51, 52, 53, 54 and 65 were prepared, namely:

(5R,6S)-6-[1(R)-hydroxyethyl]-2-[(1-methyl-1,2,3,4-tetrazol-5-yl)-thiomethyl]-penem-3-carboxylic acid;

(5R,6S)-6-[1(R)-hydroxyethyl]-2-[1-(2-cyanoethyl)-1,2,3,4-tetrazol-5-yl]-thiomethyl-penem-3-carboxylic acid;

(5R,6S)-6-[1(R)-hydroxyethyl]-2-[1-(2-cyanomethyl)-1,2,3,4-tetrazol-5-yl]-thiomethyl-penem-3-carboxylic acid;

(5R,6S)-6-[1(R)-hydroxyethyl]-2-(5-carboxymethylthio-1,3,4-(thiadiazol-2-yl)-thiomethyl-penem-3-carboxylic acid;

(5R,6S)-6-[1(R)-hydroxyethyl]-2-(5-carboxymethyl-1,3,4-thiadiazol-2-yl)-thiomethyl-penem-3-carboxylic acid;

(5R,6S)-6-[1(R)-hydroxyethyl]-2-(1-carboxymethyl-1,2,3,4-tetrazol-5-yl)-thiomethyl-penem-3-carboxylic acid;

(5R,6S)-6-[1(R)-hydroxyethyl]-2-[1(2-carboxyethyl)-1,2,3,4-tetrazol-5-yl]-thiomethyl-penem-3-carboxylic acid;

(5R,6S)-6-[1(R)-hydroxyethyl]-2-(4-carboxymethyl-5-methyl-1,3-thiazol-2-yl)-thiomethyl-penem-3-carboxylic acid;

(5R,6S)-6-[1(R)-hydroxyethyl]-2-(tetrazolo[1,5-b]pyridazin-6-yl)-thiomethyl-penem-3-carboxylic acid;

(5R,6S)-6-[1(R)-hydroxyethyl]-2-(8-carboxytetrazolo[1,5-b]pyridazin-6-yl)-thiomethyl-penem-3-carboxylic acid;

(5R,6S)-6-[1(R)-hydroxyethyl]-2-(8-aminotetrazolo[1,5-b]pyridazin-6-yl)-thiomethyl-penem-3-carboxylic acid;

(5R,6S)-6-[1(R)-hydroxyethyl]-2-[1-(2-sulfoaminoethyl)-1,2,3,4-tetrazol-5-yl]-thiomethyl-penem-3-carboxylic acid;

(5R,6S)-6-[1(R)-hydroxyethyl]-2-[1-(2-aminocarbonylethyl)-1,2,3,4-tetrazol-5-yl]-thiomethyl-penem-3-carboxylic acid;

(5R,6S)-6-[1(R)-hydroxyethyl]-2-[1-(2-aminocarbonylmethyl)-1,2,3,4-tetrazol-5-yl]-thiomethyl-penem-3-carboxylic acid;

(5R,6S)-6-[1(R)-hydroxyethyl]-2-[1-(2-dimethylaminoethyl)-1,2,3,4-tetrazol-5-yl]-thiomethyl-penem-3-carboxylic acid;

(5R,6S)-6-[1(R)-hydroxyethyl]-2-[1-(2-dimethylaminomethyl)-1,2,3,4-tetrazol-5-yl]-thiomethyl-penem-3-carboxylic acid;

(5R,6S)-6-[1(R)-hydroxyethyl]-2-(6-methoxy-pyrazin-2-yl)-thiomethyl-penem-3-carboxylic acid;

(5R,6S)-6-[1(R)-hydroxyethyl]-2-(2-amino-1,3,4-thiadiazol-5-yl)-thiomethyl-penem-3-carboxylic acid; and (5R,6S)-6-[1(R)-hydroxyethyl]-2-(1,2,3,4-tetrazol-5-yl)-thiomethyl-penem-3-carboxylic acid.

EXAMPLE 56 p-Nitrobenzyl(5R,6S)-6-[1(R)-p-nitrobenzyloxycarbonyloxyethyl]-2-(4-methyl-5-oxo-6-hydroxy-4,5-dihydro-1,2,4-triazin-3-yl)-thiomethyl-penem-3-carboxylate

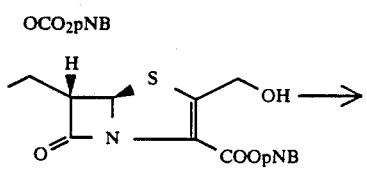

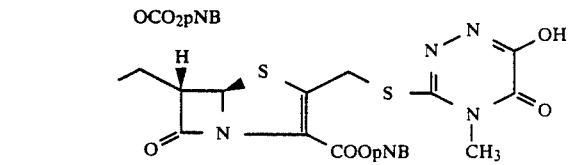

A solution of p-nitrobenzyl(5R,6S)-6-[1(R)-p-nitrobenzyloxycarbonyloxyethyl]-2-hydroxymethyl-penem-3-carboxylate (100 mg, 0.18 mmol) in dry dichloromethane (10 ml) was sequentially treated at −25° C. with triethylamine (28 μl, 0.20 mmol) and methanesulphonylchloride (14 μl, 0.18 mmol). The mixture was allowed to warm up to room temperature, then washed with diluted NaHCO₃ solution, dried (Na₂SO₄) and evaporated.

The residue was dissolved in dry THF (5 ml), treated with a second amount of triethylamine (28 μl) followed by 3-mercapto-4-methyl-5-oxo-6-hydroxy-4,5-dihydro-1,2,4-triazine (32 mg, 0.2 mmol). After 3 hours stirring at 0° C., the solvent was evaporated in vacuo and the residue chromatographed (silica gel, ethyl acetate as eluants) to afford the title product as a white solid.

IR (CHCl₃ liquid film) ν$_{max}$ 1785, 1750, 1710, 1685 cm⁻¹.

NMR (CDCl₃) δ ppm 1.46 (3H, d, J=7 Hz), 3.42 (3H, s), 3.97 (1H, dd, J=1.8 and 7.0 Hz), 4.47 (2H, ABq, J=15 Hz, separation of inner lines 7 Hz), 5.07–5.47 (5H, m), 5.60 (1H, d, J=1.7 Hz), 7.49 (2H, d, J=8.5 Hz), 7.60 (2H, d, J=8.5 Hz), 8.16 (4H, d, J=8.5 Hz).

Hydrolysis of the protecting groups as described in Example 55 lead to (5R,6S)-6-[1(R)-hydroxyethyl]-2-(4-methyl-5-oxo-6-hydroxy-4,5-dihydro-1,2,4-triazin-3-yl)-thiomethyl-penem-3-carboxylic acid.

EXAMPLE 57 p-Nitrobenzyl(5R,6S)-6-[1(R)-p-nitrobenzyloxycarbonyloxyethyl]-2-(2-aminothiazol-5-yl)-thiomethyl-penem-3-carboxylate

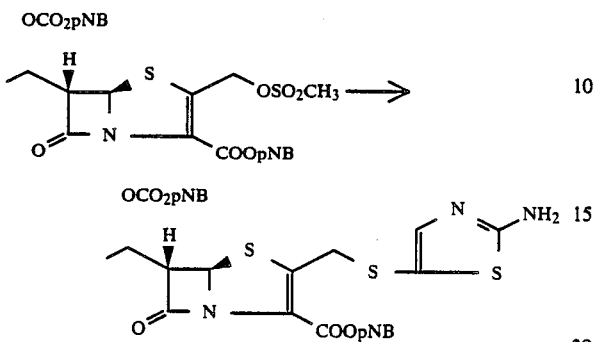

Starting from p-nitrobenzyl(5R,6S)-6-[1(R)-p-nitrobenzyloxycarbonyloxyethyl]-2-methanesulphonyloxymethyl-penem-3-carboxylate (63 mg, 0.1 mmol) and 2-amino-5-mercapto-thiazole (20 mg, 0.5 mmol), the experimental procedure described in example 56 led to the title compound (28 mg, 42%).

UV (EtOH) $\lambda_{max}$ 325 nm.

IR (nujol) $\nu_{max}$ 3200–3400, 1785, 1755, 1710.

MS (FD) m/e 673 (M+). $C_{27}H_{23}N_5O_{10}S_3$ requires M, 673.

Hydrolysis of the obtained compound according to the procedure of the Example 55 led to (5R,6S)-6-[1(R)-hydroxyethyl]-2-(2-aminothiazol-5-yl)-thiomethyl-penem-3-carboxylic acid.

EXAMPLE 58

Allyl(5R,6S)-6-[1(R)-tert-butyldimethylsilyloxyethyl]-2-methanesulphonyloxymethylpenem-3-carboxylate

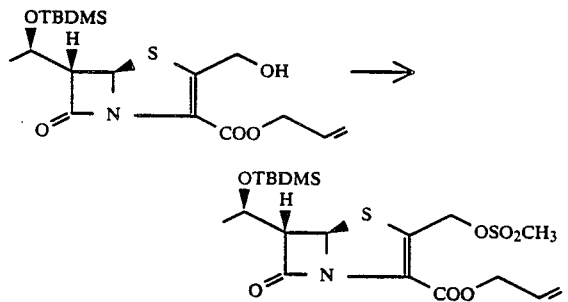

A solution of allyl(5R,6S)-6-[1(R)-tert-butyldimethylsilyloxyethyl]-2-hydroxymethylpenem-3-carboxylate (200 mg) in dry, ethanol-free dichloromethane (10 ml) was treated at −40° C. under nitrogen with triethylamine (77 µl) and then with mesyl chloride (41 µl). The temperature was let rise to 20° C., the mixture was washed with water, dried over $Na_2SO_4$, and the solvent evaporated to give an oil which is conveniently used as such for displacement reactions with sulphur nucleophiles as reported, e.g, in the following examples.

A sample purified by short-path chromatography showed the following spectral properties:

UV (CHCl$_3$) $\lambda_{max}$ 328 nm ($\epsilon$=6,249).

IR (film) $\nu_{max}$ 1793, 1710, 1590, 1360 and 1175 cm$^{-1}$.

EXAMPLE 59

Allyl(5R,6S)-6-[1(R)-tert-butyldimethylsilyloxyethyl]-2-(4-methyl-5-oxo-6-hydroxy-4,5-dihydro-1,2,4-triazin-3-yl)-thiomethyl-penem-3-carboxylate

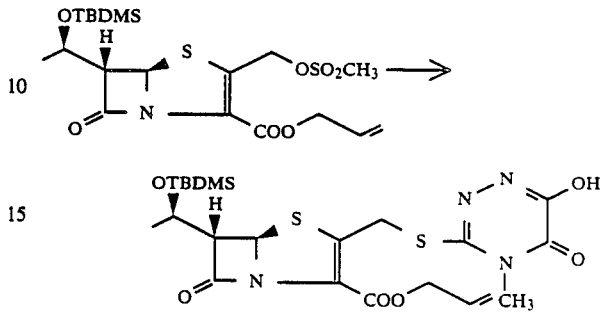

A cold solution of 6-hydroxy-3-mercapto-4-methyl-4,5-dihydro-1,2,4-triazin-5-one (100 mg) and triethylamine (0.157 ml) in tetrahydrofuran (20 ml) was added to a solution of allyl(5R,6S)-6-[1(R)-tert-butyldimethylsilyloxyethyl]-2-metanesulphonyloxymethyl-penem-3-carboxylate (240 mg) in the same solvent, and the mixture was kept overnight at approximately 0° C. The solvent was evaporated and the residue partitioned between EtOAc and water. Removal of the solvent from the dried organic extracts, followed by silica gel chromatography (ethyl acetatecyclohexane) afforded the title product as a white, amorphous solid;

UV (CHCl$_3$) $\lambda_{max}$ 280 ($\epsilon$=9,103) and 321 nm ($\epsilon$=8,738).

IR (CHCl$_3$ film) $\nu_{max}$ 3210, 1790, 1710 and 1590 cm$^{-1}$.

NMR (CDCl$_3$) δppm 0.06 (6H, s), 0.89 (9H, s), 1.22 (3H, d), 3.14–3.53 (2H, m), 3.46 (3H, s), 3.72 (1H, dd, J=2 and 4 Hz), 4.28 (1H, m), 4.50 (2H, center of ABq), 4.72 (2H, m), 5.58 (1H, d, J=2 Hz), and 11.0 (1H, broad s).

EXAMPLE 60

Allyl (5R,6S)-6-[1(R)-hydroxyethyl]-2-(4-methyl-5-oxo-6-hydroxy-4,5-dihydro-1,2,4-triazin-3-yl)-thiomethyl-penem-3-carboxylate

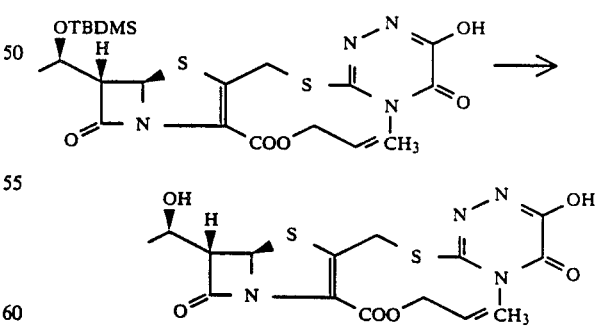

A solution of allyl (5R,6S)-6-[1(R)-tert-butyldimethylsilyloxyethyl]-2-(4-methyl-5-oxo-6-hydroxy-4,5-dihydro-1,2,4-triazin-3-yl)-thiomethyl-penem-3-carboxylate (130 mg) in tetrahydrofuran (3 ml) was treated with acetic acid (0.14 ml) and tetrabutylammonium fluoride trihydrate (228 mg). After 18 h at room temperature, the mixture was evaporated to dryness under vacuum and fractioned through a silica gel column (merck 60 HR 230–400 Mesh; φ=1.5 cm, h=12 cm). Elution with neat ethyl acetate and then with EtOAc-/EtOH 9:1 afforded the title product;

UV (EtOH) λ$_{max}$ 251 (ε=7,840) and 318 nm (ε=7,770).

IR CHCl$_3$ film) ν$_{max}$ 3400 br, 1785, 1710 br cm$^{-1}$.

NMR (CDCl$_3$) δppm 1.34 (3H, d), 3.44 (3H, s), 3.78 (1H, dd, J=2 and 6.5 Hz), 4.22 (1H, m), 4.47 (2H, broad s), 4.72 (2H, m), 5.25 and 5.40 (each 1H, broad d), 5.62 (1H, d, J=2 Hz), 5.96 (1H, m), and 11 (1H, broad s).

EXAMPLE 61

(5R,6S)-6-[1(R)-hydroxyethyl]-2-(4-methyl-5-oxo-6-hydroxy-4,5-dihydro-1,2,4-triazin-3-yl)thiomethyl-penem-3-carboxylic acid sodium salt

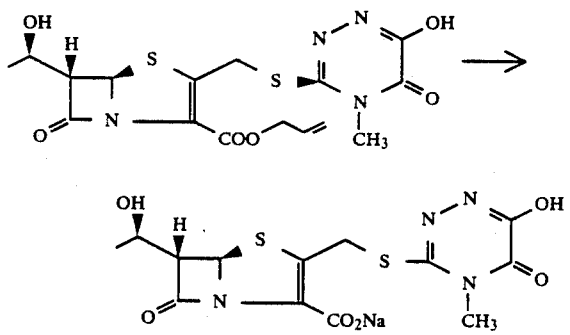

Triphenylphosphine (10 mg) and tetrakis (triphenylphosphine) palladium (0) (10 mg) were added to a solution of allyl (5R,6S)-6-[1(R)-hydroxyethyl]-2-(4-methyl-5-oxo-6-hydroxy-4,5-dihydro-1,2,4-triazin-3-yl)thiomethyl-penem-3-carboxylate (60 mg) in a 2:1 mixture of tetrahydrofuran and dichloromethane (1.5 ml). After 30 min stirring, a 0.5M solution of sodium ethylhexanoate in 1:1 tetrahydrofuran/dichloromethane (0.3 ml) was added.

The mixture was stirred for a few minutes and then let stand for 1 hour at −30° C. The precipitated solid was isolated by repeated centrifugations and washings with fresh dichloromethane, then dried under vacuum to afford 56 mg of the title product;

UV (H$_2$O) λ$_{max}$ 304 nm (ε=8,330).

IR (KBr) ν$_{max}$ 3420, 2960, 2920, 1760, 1700, 1610 and 1580 cm$^{-1}$.

EXAMPLE 62

Allyl (5R,6S)-6-[1(R)-tert-butyldimethylsilyloxyethyl]-2-(2-methyl-5-oxo-6-tert-butyldiphenylsilyloxy-2,5-dihydro-1,2,4-triazin-3-yl)-thiomethyl-penem-3-carboxylate

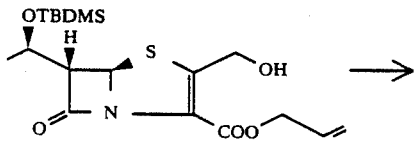

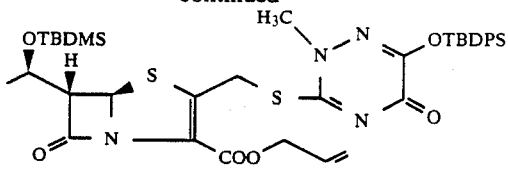

(A) A solution of 2-methyl-3-mercapto-6-hydroxy-2,5-dihydro-1,2,4-triazin-5-one (0.8 g) in dry tetrahydrofuran (25 ml) was stirred for 30 min with triethylamine (0.835 ml) and tertbutyldiphenylsilylchloride (1.53 ml). The reaction mixture was partitioned between 1% aqueous NaHCO$_3$ and ethyl acetate. Removal of the solvent from the dried organic layer left a residue which crystallized by trituration with light petrol affording 2-methyl-3-mercapto-6-tert-butyldiphenylsilyloxy-2,5-dihydro-1,2,4-triazin-5-one (1.34 g), m.p. 135° C. (decomp.);

UV (CHCl$_3$) λ$_{max}$ 276 (ε=20,820) and 320 sh (=4,460) nm

IR (CHCl$_3$) ν$_{max}$ 1720, 1580 cm$^{-1}$.

NMR (CDCl$_3$) δppm 1.1 (9H, s), 3.4 (3H, s), 7.2–7.7 (10H, m), 9.9 (1H, br s).

(B) A solution of triphenylphosphine (472 mg) in dry distilled THF (12 ml) was treated at 0° C. with ethyl azodicarboxylate (282 μl, dissolved in 2 ml of the same solvent). After 1 hour stirring at 0° C., this solution was added under stirring to a solution of the product obtained under (A) (630 mg) and of allyl (5R,6S)-6-[1(R)-tert-butyldimethylsilyloxyethyl]-2-hydroxymethyl-penem-3-carboxylate (600 mg) in dry distilled THF (6 ml).

Soon at the end of the addition the reaction was over (tlc monitoring, SiO$_2$, EtOAc/C$_6$H$_{12}$ 1:2); the solvent was removed and the crude material was freed from some polar contaminants by flash chromatography (SiO$_2$, ethyl acetate-cyclohexane), thus obtaining 1 g of the title product;

UV (CHCl$_3$) λ$_{max}$ 333 nm;

IR (CHCl$_3$ film) ν$_{max}$ 1787, 1705, 1665 cm$^{-1}$.

NMR (CDCl$_3$) δ$_{ppm}$ (inter alia) 3.30 (3H, s), 3.66 (1H, dd), 4.20 (1H, m), 4.65 (4H, m), 5.15–5.50 (2H, m), 5.54 (1H, d), 5.70–6.15 (1H, m).

EXAMPLE 63

Allyl (5R,6S)-6-[1(R)-hydroxyethyl]-2-(2-methyl-5-oxo-6-hydroxy-2,5-dihydro-1,2,4-triazin-3-yl)thiomethyl-penem-3-carboxylate

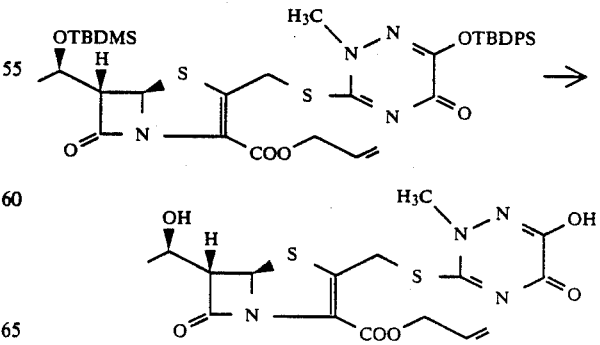

The bis-silylated material obtained in Example 62 (1 g), dissolved in dry tetrahydrofuran (16 ml) was stirred for 22 hours at room temperature in the presence of acetic acid (0.76 ml) and tetrabutylammonium fluoride trihydrate (1.26 g). The solvent was removed in vacuo, the residue taken up in a small amount of water ($\leq 10$ ml) and passed through a reverse-phase column (Merck LiChroprep RP-18; $\phi 2$ cm, h=10 cm), eluting first with water, then with H$_2$O/EtOH 4:1 and finally with H$_2$O/EtOH 2:1. The title product was obtained from the last fractions by removal of the ethanol followed by freeze-drying (350 mg);

IR (CHCl$_3$ film) $\nu_{max}$ 3400 br, 1750, 1700 br cm$^{-1}$.

EXAMPLE 64

(5R,6S)-6-[1(R)-hydroxyethyl]-2-(2-methyl-5-oxo-6-hydroxy-2,5-dihydro-1,2,4-triazin-3-yl)thiomethyl-penem-3-carboxylic acid, disodium salt

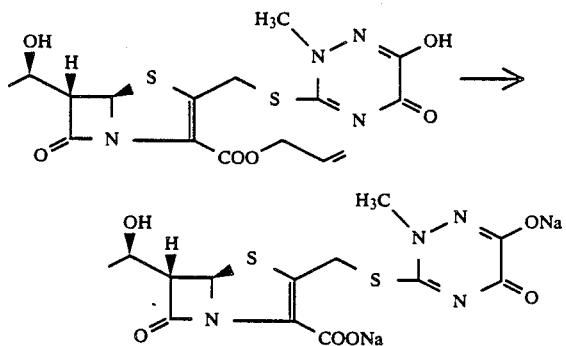

A solution of allyl (5R,6S)-6-[1(R)-hydroxyethyl]-2-(2-methyl-5-oxo-6-hydroxy-2,5-dihydro-1,2,4-triazin-3-yl)thiomethyl-penem-3-carboxylate (300 mg) in a mixture of tetrahydrofuran (5 ml) and dichloromethane (2 ml) was treated under stirring with triphenylphosphine (30 mg) and tetrakis (triphenylphosphine) palladium (O) (30 mg), soon followed by a 0.5M solution of sodium ethylhexanoate in 1:1 THF/CH$_2$Cl$_2$ (2.86 ml). The white precipitate was collected by centrifugation, triturated in CH$_2$Cl$_2$ and centrifugated again (twice), then dissolved in a small amount of water and passed through a reverse-phase column (Merck LiChroprep RP-18) eluting with distilled water. The product-containing fractions (Merck Kieselgel 60 F 254 silanisiert, CHCl$_3$/CH$_3$OH/HCOOH 90:15:10; Rf=0.3) were collected and evaporated to affored the title product;

UV $\lambda_{max}$ 277 and 308 (sh) nm;

IR (KBr) $\nu_{max}$ 3420, 2960, 2920, 1760, 1640 and 1605 cm$^{-1}$;

NMR (D$_2$O) (200 MHz apparatus) $\delta_{ppm}$ 1.25 (3H, d), 3.65 (3H, s), 3.82 (1H, dd), J=1.6 and 5.9 Hz), 4.20 (1H, m), 4.59 (2H, ABq, J=14.5 Hz, separation of inner lines 14.9 Hz), 5.55 (1H, d, J=1.6 Hz).

EXAMPLE 65

By starting from the appropriate precursors, and following the experimental procedure described in Examples 58–61 (method A in the following table) or the one described in Examples 62–64 (method B in the table), the herebelow tabulated compounds were obtained:

| Code number | R | Method | UV, nm $\lambda$max (H$_2$O) | IR, cm$^{-1}$ $\nu$max (KBr) | NMR (D$_2$O), $\delta$ppm |
|---|---|---|---|---|---|
| FCE 22752 | N-N=N-N(CH$_2$CO$_2$Na) | A[1] | 315 | — | same data reported in example 45. |
| FCE 22753 | N-N=N-N(CH$_2$CH$_2$CO$_2$Na) | A[1] | 314 | 3600–3200, 2960,2920, 2870,1765, 1580,1390 | same data reported in example 46 |
| FCE 22859[2] | N-N=N-N(CH$_2$CH$_2$NH(CH$_3$)CH$_3$) | A | 315 | 1765,1630 broad | 1.29(3H,d),2.93 (6H,s),3.73(2H,t), 3.88(1H,dd,J=2 and 4.5Hz),4.25 (1H,m),4.57(2H,ABq) 4.90(2H,t),5.64 (1H,d,J=2Hz) |
| FCE 22754 | (pyridazine-fused triazine) | A | 312 | 3430,3080, 3040,2960, 2920,2850, 1765,1605, 1570 | 1.24(3H,d),3.82 (1H,dd,J=1.5 and 6.1Hz),4.22(1H,m), 4.66 and 4.96(each 1H,d,J=12Hz),5.60 (1H,d,J=1.5Hz),7.68 and 8.38 (each 1H, d,J=9.6Hz) |

-continued

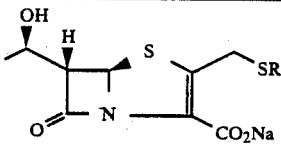

| Code number | R | Method | UV, nm λmax (H2O) | IR, cm$^{-1}$ νmax (KBr) | NMR (D2O), δppm |
|---|---|---|---|---|---|
| FCE 22846[3] | 4-amino-pyridazino-tetrazole | A | 299 | 3500–3150, 1760,1660, 1625,1570 | 1.30(3H,d),3.77 (1H,dd,J=1.8 and 6.5Hz),4.18(1H, m),4.55(2H,br s), 5.50(1H,d,J=1.8Hz) 6.50(1H,s) |
| FCE 22864[3] | methylpyridine-OCH3 | A | 326 | 3430,3040, 2960,2920, 2860,1765, 1620,1570, 1550,1520, 1490 | 1.38(3H,d),3.77 (1H,dd),3.97(3H, s),4.3(1H,m),4.60 (2H,ABq),5.55(1H, d),7.83–8.03(2H,m) |
| AM 5441/25[3] | thiadiazole-CH3 | A | — | 3430,2960, 2920,2860, 1765,1570 | 1.37(3H,d),2.77 (3H,s),3.87(1H,dd), 4.30(1H,m),4.62 (2H,ABq),5.62(1H,d) |
| FCE 22923[3] | thiadiazole-NH2 | A | — | 3420,3300, 3180,2960, 2920,2860, 1765,1560 | 1.38(3H,d),3.92(1H, dd),4.28(1H,m), 4.42(2H,s),5.64 (1H,d) |
| AM 5441/56[3] | triazole-NH | B | 314 | 1765,1605 | — |
| FCE 22988[3] | triazole-CH2CH2CONH2 | B | 315 | 3400,1770, 1695,1610 | — |
| FCE 22862[3] | triazole-CH2CH2CN | A | 316 | 3430,2960, 2920,2850, 2250,1765, 1615 | 1.26(3H,d),3.23 (2H,t),3.84(1H, dd,J=1.4 and 6Hz),4.20(1H,m), 4.54(2H,ABq,J=14.2 Hz, sep. of inner lines 12Hz),4.8 (2H,t),5.58(1H,d, J=1.4Hz) |

[1] During the synthesis, the carboxy group on the heterocyclic thiol was protected as its allyl ester.
[2] Isolated as the internal salt with the 3-penemcarboxylate anion.
[3] Isolated as the potassium salt, by using potassium ethylhexanoate.

EXAMPLE 66

Following analogous procedure as the one dscribed in examples 58 to 61, the herebelow listed compounds were synthesized: (5R,6S)-6-[1(R)-hydroxyethyl]-2-(1-methylimidazol-2-yl)-thiomethyl-penem-3-carboxylic acid, isolated as the sodium salt;

UV (H2O) λ$_{max}$ 315 nm;

NMR (200 MHz, D2O) δ$_{ppm}$ 1.21 (3H, d, J=6.4 Hz), 3.72 (3H, s), 3.76 (1H, dd, J=1.4 and 6 Hz), 4.13 (2H, ABq, J=14 Hz, separation of inner lines 36 Hz), 4.14 (1H, m), 5.51 (1H, d, J=1.4 Hz), 7.04 and 7.21 (each 1H, d, J=1.3 H);

(5R,6S)-6-[1(R)-hydroxyethyl]-2-[1-(1,2,3,4-tetrazol-5-yl)-methyl-1,2,3,4-tetrazol-5-yl]-thiomethyl-penem-3-carboxylic acid, isolated as the sodium salt;

UV (H2O) λ$_{max}$ 256 and 314 nm.

By replacing sodium ethylhexanoate with a molar excess of acetic acid, the aforementioned compounds were isolated as the free acids. Moreover, the following ones were also prepared:

(5R,6S)-6-[1(R)-hydroxyethyl]-2-(3-amino-1,2,4-triazol-5-yl)-thiomethyl-penem-3-carboxylic acid;

UV (H2O) λ$_{max}$ 262 and 310 nm; and (5R,6S)-6-[1(R)-hydroxyethyl]-2-(1,2,3-thiadiazol-5-yl)-thiomethyl-penem-3-carboxylic acid;

UV (H2O) λ$_{max}$ 330 nm;

MS (FD) m/e 345 (M+) $C_{11}H_{11}N_3O_4S_3$ requires M 345.

EXAMPLE 67

Allyl (5R,6S)-6[1(R)-tert-butyl-dimethylsilyloxyethyl]-2-(1,2,4-triazol-5-yl)thiomethyl-penem-3-carboxylate

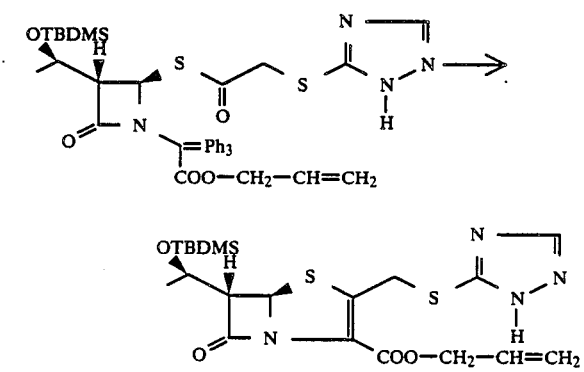

A solution of 4(R)-(1,2,4-triazol-5-yl)-thioacetylthio-3(S)-1(R)-tert-butyl-dimethylsilyloxyethyl)-1-(1-allyloxycarbonyl)-1-triphenylphosphoranylidenemethyl)-azetidin-2-one (0.45 g) in toluene (50 ml) was refluxed under nitrogen atmosphere for three hours.

Short column chromatography on silica gel with dichloromethane:ethylacetate (8:2) as eluant gave 0.25 g of pure title compound;

NMR (CDCl₃), δppm=0.06 (6H, s), 0.89 (9H, s), 1.35 (3H, d, J=7 Hz) 3.88 (1H, dd, J=2 and 5 Hz), 4.25 (1H, m), 4.6 (4H, m), 5.1–5.4 (2H, m), 5.50 (1H, d, J=2Hz), 5.6–6.1 (1H, m), 8.17 (1H, br s).

EXAMPLE 68

Allyl (5R,6S)-6-[1(R)-hydroxyethyl]-2-(1,2,4-triazol-5-yl)-thiomethyl-penem-3-carboxylate

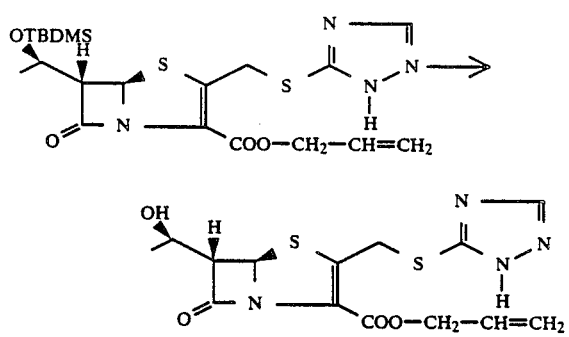

A solution of the compound obtained in example 67 (0.380 g) in tetrahydrofuran (8 ml) was treated with acetic acid (0.5 ml) and tetrabutylammonium fluoride trihydrate (0.69 g) until the starting material had disappeared (tlc monitoring) (14–24 hrs). The reaction mixture was evaporated in vacuo and then chromatographed (SiO₂ column, ethyl acetate-cyclohexane mixtures) thus obtaining the title compound;

IR (CHCl₃ film) 3380 br, 1785, 1715 cm⁻¹.

EXAMPLE 69

(5R,6S)-6-[1(R)-hydroxyethyl]-2-(1,2,4-triazol-5-yl)thiomethyl-penem-3-carboxylic acid, sodium salt

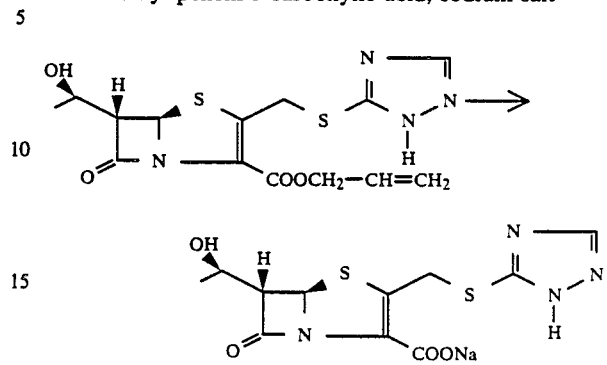

A solution of the ally ester obtained in example 68 (0.2 g) in tetrahydrofuran (1 ml) was sequentially treated with triphenylphosphine (0.07 g) and tetrakis(triphenylphosphine)palladium (0) (0.07 g), followed after a few minutes by a 0.5M solution of sodium ethylhexanoate in 1:1 THF/dichloromethane (2.1 ml). After 15 min stirring, ethyl ether was added to precipitate the title compound as a yellowish powder, which was collected by filtration, washed several times with dichloromethane and vacuum-dried; UV (H₂O) λmax 314 nm; IR (KBr) γmax 1765 and 1620 br cm⁻¹.

Operating in analogous way and starting from the appropriate intermediates obtained according to the procedure described in the examples 67 and 68, also the compounds mentioned in the examples 38, 42, 44, 48, 49, 56, 57, 65 and 66 were prepared.

EXAMPLE 70

Acetoxymethyl(5R,6S)-6-[1(R)-hydroxyethyl]-2-(1-methyl-1,2,3,4-tetrazol-5-yl)thiomethylpenem-3-carboxylate

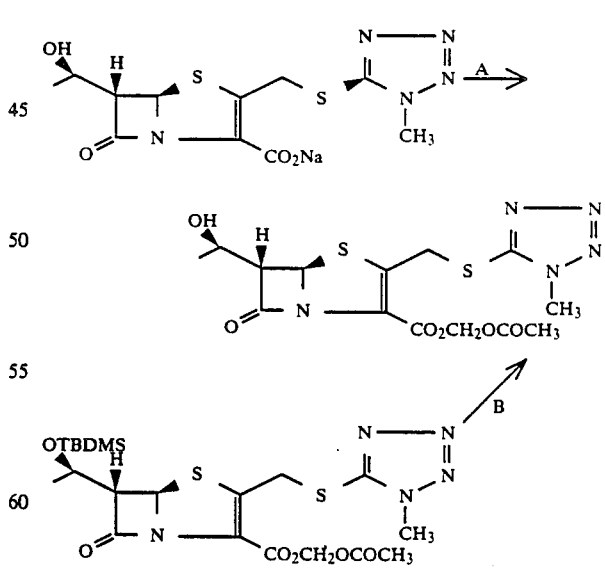

(A) A solution of sodium(5R,6S)-6-[1(R)-hydroxyethyl]-2-(1-methyl-1,2,3,4-tetrazol-5-yl)thiomethylpenem-3-carboxylate (3.1 g) in dry dimethylformamide (25 ml) was kept overnight in the presence of bromomethyl acetate (2.2 g). After further 2 hours at room temperature, the reaction mixture was partitioned between brine and ethyl acetate. After several washings with brine, the organic phase was dried and evaporated to a residue which was triturated with ethyl ether/light petrol, thus obtaining the title compound as a white powder;

IR (KBr) 1795, 1760, 1720 cm⁻¹.

NMR (acetone d-6), δppm (inter alia): 1.25 (3H, d), 2.06 (3H, s), 3.75 (1H, dd), 5.83 (2H, ABq), 5.69 (1H, d, J=1.5 Hz).

(B) A solution of acetoxymethyl(5R,6S)-6-[1(R)-tert-butyldimethylsilyloxyethyl]-2-(1-methyl-1,2,3,4-tetrazol-5-yl)thiomethylpenem-3-carboxylate, (1 g) [obtained as described in Example 30] in dry THF₁ was stirred for 20 hours at room temperature in the presence of acetic acid (1 ml) and tetrabutylammonium fluoride (1.5 g). Removal of the solvent and partition between ethyl acetate and water, followed by evaporation, furnished the title compound.

EXAMPLE 71

Following analogous procedure to the one described under (A) in Example 70, or the one described in Example 30 and Example 70 under (B), the herebelow listed compounds were obtained:

acetoxymethyl(5R,6S)-6-[1(R)-hydroxyethyl]-2-(1,2,3-thiadiazol-5-yl)thiomethylpenem-3-carboxylate;

acetoxymethyl(5R,6S)-6-[1(R)-hydroxyethyl]-2-(2-methyl-5-oxo-6-hydroxy-2,5-dihydro-1,2,4-triazin-3-yl)thiomethylpenem-3-carboxylate; and acetoxymethyl(5R,6S)-6-[1(R)-hydroxyethyl]-2-(tetrazolo[1,5-b]pyridazin-6-yl)thiomethylpenem-3-carboxylate.

EXAMPLE 72

Allyl(5R,6S)-6-[1(R)-tert-butyldimethylsilyloxyethyl]-2-(2-p-nitrobenzyloxycarbonylaminoethyl)thiomethylpenem-3-carboxylate

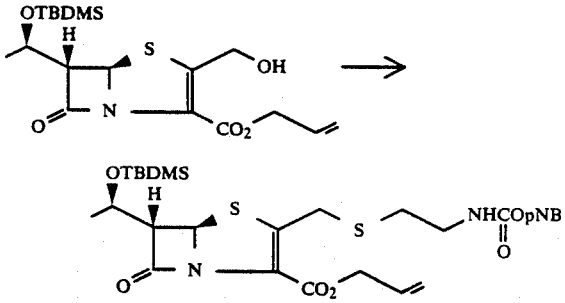

Triphenylphosphine (131 mg, 0.5 mmol) and diethylazodicarboxylate (78 μl, 0.5 mmol) in 1.8 ml of dry distilled tetrahydrofuran were allowed to react for 30 min at 0° C. To this mixture, allyl(5R,6S)-6-[1(R)-tert-butyldimethylsilyloxyethyl]-2-hydroxymethylpenem-3-carboxylate (100 mg, 0.25 mmol) in THF (5 ml), soon followed by cysteamine p-nitrobenzylcarbonate (100 mg, 0.4 mmol) were added. The mixture was let rise to room temperature while stirring. After 30 min, the solvent was removed in vacuo and the residue was chromatographed (silica gel, ethyl acetate-cyclohexane) to afford the title product as a yellowish syrup.

IR (film) νmax 1790, 1750, 1710 cm⁻¹.

NMR (CDCl₃) δppm 0.06 (6H, s), 0.94 (9H, s), 1.32 (3H, d), 2.56 (2H, t, J=7 Hz), 3.40 (2H, t of doublets, J=7 Hz), 3.85 (1H, dd, J=2 and 6.5 Hz), 4.0–4.3 (3H, m), 4.65 (2H, m), 5.1–5.4 (2H, m), 5.25 (2H, s), 5.60 (1H, d, J=2 Hz), 5.70–6.15 (1H, m), 7.60 and 8.30 (each 2H, d, J=9 Hz) ppm.

EXAMPLE 73

Sodium(5R,6S)-6-[1(R)-hydroxyethyl]-2-(2-aminoethyl)-thiomethylpenem-3-carboxylate

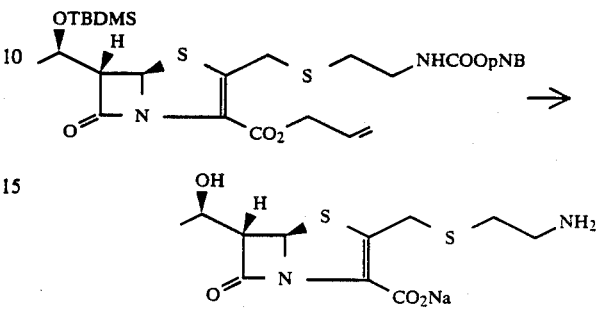

A solution of allyl(5R,6S)-6-[1(R)tert-butyldimethylsilyloxyethyl]-2-(2-p-nitrobenzyloxycarbonylaminoethyl)thiomethylpenem-3-carboxylate (150 mg, 0.23 mmol) in THF (2 ml) was stirred for 24 hours with acetic acid (100 μl) and tetrabutylammonium fluoride (165 mg). Removal of the solvent and short-path chromatography yielded allyl(5R,6S)-6-[1(R)-hydroxyethyl]-2-(2-p-nitrobenzyloxycarbonylaminoethyl)thiomethylpenem-3-carboxylate in almost quantitative yield. This material was dissolved in a mixture of THF (1 ml) and dichloromethane (1 ml), then triphenylphosphine (8 mg) and tetrakis-triphenylphosphine-Pd(0) (8 mg), were added under argon, soon followed by sodium ethylhexanoate (36 mg). After 5 min stirring, the mixture was diluted with ethyl ether and filtered, thus collecting sodium(5R,6S)-6-[1(R)-hydroxyethyl]-2-(2-p-nitrobenzyloxycarbonylaminoethyl)thiomethylpenem-3-carboxylate (70 mg) as a white powder. This compound was directly dissolved in a mixture of THF (5 ml) and of pH 7.0 phosphate buffer (5 ml) and shaken in a hydrogen atmosphere with 10% Palladium on charcoal (two portions, 50 mg each, added at 15 min interval). The catalyst was filtered off, the liquors were washed with ethyl acetate and the aqueous phase was concentrated in vacuo and then chromatographed on a reverse-phase column, eluting with water. The product-containing fractions (UV, λmax 314 nm) were collected and freeze-dried, thus obtaining 20 mg of the title product:

IR (KBr) νmax 1770, 1610 cm⁻¹,
UV (H₂O) λmax 314 nm.

EXAMPLE 74

Reaction of allyl(5R,6S)-6-[1(R)-tert-butyldimethylsilyloxyethyl]-2-hydroxymethylpenem-3-carboxylate with the appropriate heterocyclic thiol and the preformed complex between triphenylphosphine and diethylazodicarboxylate, followed by sequential cleavage of the silyloxy and allyloxy protecting groups, according to the general methodologies illustrated in the foregoing examples, afforded:

potassium(5R,6S)-6-[1(R)-hydroxyethyl]-2-(pyrazin-2-yl)thiomethylpenem-3-carboxylate; UV (H₂O) λmax 250 (ε=10,344) and 319 (ε=8,682) nm; IR (KBr) νmax 3400, 1760, 1600 cm⁻¹; NMR (D₂O) δppm 1.26 (3H, d, J=6.5 Hz), 3.07 (1H, dd, J=1 and 4 Hz), 4.2 (1H, m), 4.54 (2H, s), 5.47 (1H, d, J=1 Hz), 8.32–8.06 (3H, m, Ar);

potassium(5R,6S)-6-[1(R)hydroxyethyl]-2-(4-ethyl-1,3,4-triazol-3-yl)thiomethylpenem-3-carboxylate; UV (H₂O) νmax 316 nm (ε=5,600); IR (KBr) νmax 3420, 1765, 1600 cm⁻¹; NMR (D₂O) δppm 1.26 (3H, d, J=6.6 Hz), 1.42 (3H, t, J=5.6 Hz), 3.77 (1H, dd, J=1.6 and 8.1 Hz), 4.17 (2H, q, J=5.6 Hz), 4.2 (1H, m), 4.2 and 4.43 (2H, each d, J=14 Hz), 5.52 (1H, d, J=1.6 Hz), 8.55 (1H, s); (5R,6S)-6-[1(R)-hydroxyethyl]-2-(5-carboxymethylthio-1,3,4-thiadiazol-2-yl)thiomethylpenem-3-carboxylic acid, dipotassium salt; IR (KBr) νmax 3380, 1755, 1610 cm⁻¹; NMR (D₂O) δppm 1.25 (3H, d), 3.85 (1H, dd, 1.5 and 6 Hz), 3.97 (2H, s), 4.2 (1H, m), 4.55 (2H, s), 5.57 (1H, d, J=1.5 Hz).

We claim:
1. A compound of the following formula (Ia):

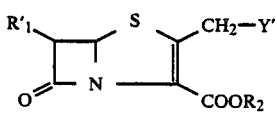 (Ia)

wherein
R'₁ is a C₁–C₆ alkyl group substituted by hydroxy;
R₂ is hydrogen;
Y' is a group —S-Het' wherein Het' represents:
(a) 5-oxo-6-hydroxy-2,5-dihydro-1,2,4-triazinyl or 5-oxo-6-hydroxy-4,5-dihydro-1,2,4-triazinyl, both optionally substituted by a C₁–C₃ alkyl group; or
(b) tetrazolo-pyridazinyl optionally substituted by a group

wherein each of R' and R" is independently hydrogen or C₁–C₃ alkyl group; and the pharmaceutically acceptable salts thereof.

2. A compound having the formula (Ia) reported above in claim 1 wherein R'₁ is α-hydroxyethyl, and the pharmaceutically acceptable salts thereof.

3. A compound of formula (Ia) according to claim 2 wherein the said compound is the (5R,6S) isomer and wherein the carbon atom carrying the hydroxy group in the α-hydroxyethyl moiety is in the R configuration.

4. A compound selected from the group consisting of
(5R,6S)-6-[1(R)-hydroxyethyl]-2-(tetrazolo[1,5-b]pyridazin-6-yl)-thiomethyl-penem-3-carboxylic acid;
(5R,6S)-6-[1(R)-hydroxyethyl]-2-(8-aminotetrazolo[1,5-b]pyridazin-6-yl)-thiomethyl-penem-3-carboxylic acid;
(5R,6S)-6-[1(R)-hydroxyethyl]-2-(2-methyl-5-oxo-6-hydroxy-2,5-dihydro-1,2,4-triazin-3-yl)-thiomethyl-penem-3-carboxylic acid;
(5R,6S)-6[1(R)-hydroxyethyl]-2-(4-methyl-5-oxo-6-hydroxy-4,5-dihydro-1,2,4-triazin-3-yl)-thiomethyl-penem-3-carboxylic acid;
and the pharmaceutically acceptable salts thereof.

5. An antibacterial pharmaceutical composition containing a suitable carrier and/or diluent and, as an active principle, an antibacterially effective amount of a compound of formula (Ia) as reported in claim 1 or a pharmaceutically acceptable salt thereof.

6. A salt of a compound according to any one of claims 1 to 4 wherein the salt is an alkali metal salt.

7. An alkali metal salt according to claim 6 wherein the alkali metal is sodium or potassium.

8. The compound of claim 1, where Het' represents 5-oxo-6-hydroxy-2,5-dihydro-1,2,4-triazinyl or 5-oxo-6-hydroxy-4,5-dihydro-1,2,4-triazinyl, both optionally substituted by a C₁–C₃ alkyl group.

9. The compound of claim 2, where Het' represents 5-oxo-6-hydroxy-2,5-dihydro-1,2,4-triazinyl or 5-oxo-6-hydroxy-4,5-dihydro-1,2,4-triazinyl, both optionally substituted by a C₁–C₃ alkyl group.

* * * * *

UNITED STATES PATENT AND TRADEMARK OFFICE
CERTIFICATE OF CORRECTION

PATENT NO. : 4,729,990

DATED : Mar. 8, 1988

INVENTOR(S) : Marco Alpegiani, et al.

It is certified that error appears in the above-identified patent and that said Letters Patent is hereby corrected as shown below:

On the Title Page, Item [75]

The name of the fourth inventor should read as follows:

-- Giovanni Franceschi --

Signed and Sealed this

Ninth Day of August, 1988

Attest:

DONALD J. QUIGG

Attesting Officer

Commissioner of Patents and Trademarks